(12) United States Patent
Lee et al.

(10) Patent No.: US 11,096,612 B2
(45) Date of Patent: Aug. 24, 2021

(54) METHODS OF PERSONALIZED MICROFILTRATION TO DETECT CELLS FROM BLOOD

(71) Applicant: The Hong Kong University of Science and Technology, Hong Kong (CN)

(72) Inventors: Yi-Kuen Lee, Hong Kong (CN); Cong Zhao, Hong Kong (CN); Kashif Riaz, Hong Kong (CN)

(73) Assignee: The Hong Kong University of Science and Technology, Hong Kong (CN)

( * ) Notice: Subject to any disclaimer, the term of this patent is extended or adjusted under 35 U.S.C. 154(b) by 135 days.

(21) Appl. No.: 16/097,042

(22) PCT Filed: Apr. 26, 2017

(86) PCT No.: PCT/CN2017/082043
§ 371 (c)(1),
(2) Date: Oct. 26, 2018

(87) PCT Pub. No.: WO2017/186129
PCT Pub. Date: Nov. 2, 2017

(65) Prior Publication Data
US 2019/0142322 A1     May 16, 2019

Related U.S. Application Data

(60) Provisional application No. 62/328,171, filed on Apr. 27, 2016.

(30) Foreign Application Priority Data

Aug. 29, 2016  (CN) .......................... 201610753136.9

(51) Int. Cl.
*G01N 33/574*     (2006.01)
*G01N 33/50*      (2006.01)
(Continued)

(52) U.S. Cl.
CPC ....... *A61B 5/150755* (2013.01); *C12M 47/04* (2013.01); *C12N 5/0694* (2013.01);
(Continued)

(58) Field of Classification Search
CPC ............. A61B 5/150755; C12M 47/04; C12N 5/0694; G01N 15/1031; G01N 33/5094;
(Continued)

(56) References Cited

U.S. PATENT DOCUMENTS 8,114,289 B2 *  2/2012  Zheng .................... B01D 71/28
                                                210/321.84
8,986,945 B2 *  3/2015  Lin ..................... G01N 33/5094
                                                435/30

(Continued)

FOREIGN PATENT DOCUMENTS

CN         105087775 A     11/2015

OTHER PUBLICATIONS

Kim et al. Small, vol. 9, No. 18, 2013, pp. 2103-2110.*
(Continued)

*Primary Examiner* — Maureen Wallenhorst
(74) *Attorney, Agent, or Firm* — Osha Bergman Watanabe & Burton LLP

(57) ABSTRACT

The present application provides a Capillary number-based method of isolating circulating rare cells from a blood sample from a subject using filtration parameters determined based on the measurement of hemorheological parameters of the sample. The present application also provides a method for determining filtration parameters in a microfluidic elasto-filtration process for isolating circulating rare cells from a blood sample from a subject. The present application further provides a device for isolating circulating rare cells from a
(Continued)

blood sample from a subject and a non-transitory computer storage medium for performing methods described in the present application.

14 Claims, 14 Drawing Sheets

(51) Int. Cl.
  *G01N 15/10* (2006.01)
  *C12N 5/09* (2010.01)
  *A61B 5/15* (2006.01)
  *C12M 1/00* (2006.01)
(52) U.S. Cl.
  CPC ..... *G01N 15/1031* (2013.01); *G01N 33/5094* (2013.01); *G01N 33/574* (2013.01)
(58) Field of Classification Search
  CPC ............... G01N 33/574; Y10T 436/25; Y10T 436/25125; Y10T 436/25375; Y10T 436/255
  USPC ................ 436/63, 149, 174, 175, 177, 178; 422/527, 534, 535; 435/29, 34
  See application file for complete search history.

(56) References Cited

U.S. PATENT DOCUMENTS

| | | | |
|---|---|---|---|
| 10,416,150 B2 * | 9/2019 | Soper | B01L 3/5027 |
| 2012/0178097 A1 | 7/2012 | Tai et al. | |
| 2017/0072396 A1 * | 3/2017 | Takagi | G01N 1/4077 |

OTHER PUBLICATIONS

Zhao et al. MEMS, Estoril, Portugal, Jan. 18-22, 2015, pp. 459-462.*
Zhao C. et al., "Isolation of circulating tumor cells under hydrodynamic loading using microfluidic technology", Advances in Mechanics, 2014, 44: 201412 (48 pages).
Yusa A. et al., "Development of a New Rapid Isolation Device for Circulating Tumor Cells (CTCs) Using 3D Palladium Filter and Its Application for Genetic Analysis", PLoS ONE, Feb. 2014, vol. 9, Issue 2, pp. 1-11 (11 pages).
Asghar W. et al., "Electrical fingerprinting, 3D profiling and detection of tumor cells with solid-state micropores", Lab Chip, Mar. 2012, 12, pp. 2345-2352 (8 pages).
Adams D. et al., "Cytometric Characterization of Circulating Tumor Cells Captured by Microfiltration and Their Correlation to the CellSearch® CTC Test", Cytometry Part A, 2015, vol. 87A, pp. 137-144 (8 pages).
Desitter I. et al., "A New Device for Rapid Isolation by Size and Characterization of Rare Circulating Tumor Cells", Anticancer Research, 31, 2011, pp. 427-442 (15 pages).
Adams D. et al., "The systematic study of circulating tumor cell isolation using lithographic microfilters", RSC Adv., 2014, 4, pp. 4334-4342 (9 pages).
International Search Report and Written Opinon issued in corresponding International Application No. PCT/CN2017/082043 dated Aug. 3, 2017 (6 pages).

A. Pinkowski, et al., "A Hydrodynamic Approach to Cancer", bioRxiv, Feb. 2015 (18 pages).
C. E. Omoti, et al., "Haemorheological Changes in Cancer Patients on Chemotherapy", Pak J Med Sci, Jun. 2007, vol. 23, No. 3, pp. 313-317 (5 pages).
C. T. Lim, et al., "Microdevice for the isolation and enumeration of cancer cells from blood", Biomed Microdevices, 2009, 11:883-892 (10 pages).
D. L Adams, et al., "The systematic study of circulating tumor cell isolation using lithographic microfilters", RSC Advances, 2014, 9, pp. 1-20 (20 pages).
F. A. W. Coumans, et al., "Filter Characteristics Influencing Circulating Tumor Cell Enrichment from Whole Blood", PLos ONE, 2013, 8(4): e61770 (12 pages).
F. A. W. Coumans, et al. "Filtration Parameters Influencing Circulating Tumor Cell Enrichment from Whole Blood", PLos ONE, 2013, 8(4): e61774 (9 pages).
G. Vona, et al., "A New Method for the Immunomorphological and Molecular Characterization of Circulating Tumor Cells", American Journal of Pathology, vol. 156, No. 1, Jan. 2000, pp. 57-63 (7 pages).
George-Friedrich von Tempelhoff, et al., "Prognostic role of plasmaviscosity in breast cancer", Clinical Hemorheology and Microcirculation, 2002, pp. 55-61 (7 pages).
H. Mohamed, et al., "Isolation of tumor cells using size and deformation", Journal of Chromatography A, 2009, pp. 8289-8295 (7 pages).
L. M. Maestro, et al., "Circulating Tumor Cells in Solid Tumor in Metastatic and Localized Stages", Anticancer Research 29, 2009, pp. 4839-4843 (5 pages).
L. S. Lim, et al. "Microsieve lab-chip device for rapid enumeration and fluorescence in situ hybridization of circulating tumor cells", Lab Chip, 2012, 12, pp. 4388-4396 (9 pages).
M. Hoskawa, et al., "Size-Selective Microcavity Array for Rapid and Efficient Detection of Circulating Tumor Cells", Analytical Chemistry, 2010, 82, pp. 6629-6635 (7 pages).
M. Khan, et al. "Hemorheologicial Profiles in Cancer Patients", Clinical Hemorheology, vol. 15, No. 1, 1995, pp. 37-44 (8 pages).
R. A. Harouaka, et al., "Flexible Micro Spring Array Device for High-Throughput Enrichment of Viable Circulating Tumor Cells", Clinical Chemistry, 60:2, 2014, pp. 323-333 (11 pages).
S. Zheng, et al., "Membrane microfilter device for selective capture, electrolysis and genomic analysis of human circulating tumor cells", Journal of Chromatography A, 1162, 2007, pp. 154-161 (8 pages).
S. J. Tan, et al., "Versatile label free biochip for the detection of circulating tumor cells from peripheral blood in cancer patients", Biosensors and Bioelectronics 26, 2010, pp. 1701-1705 (5 pages).
S. O. Elusoji, et al., "Haemorheological Changes in African Breast Cancer Patients", African Journal of Reproductive Health, vol. 12, No. 1, Apr. 2008, pp. 84-89 (6 pages).
W. J. Allard et al., "Tumor Cells Circulate in the Peripheral Blood of All Major Carcinomas but not in Healthy Subjects or Patients with Nonmalignant Diseases", Clincial Cancer Research, Oct. 2004, vol. 10, pp. 6897-6904 (8 pages).
Z. Zhang et al., "The effects of 3D channel geometry on CTC passing pressure—towards deformability-based cancer cell separation", Lab on a Chip, 2014, 00, pp. 1-8 (10 pages).
M. Hoskawa, et al., "Size-Based Isolation of Circulating Tumor Cells in Lung Cancer Patients Using a Microcavity Array System", PLos ONE, 2013, 8(6): e67466 (9 pages).

* cited by examiner

Exemplary "Capillary Number based Microfluidic Elasto-Filtration" method

METHODS OF PERSONALIZED MICROFILTRATION TO DETECT CELLS FROM BLOOD

CROSS REFERENCE

The present application claims priorities to provisional U.S. patent application No. 62/328,171 filed on Apr. 27, 2016, and Chinese patent application No. 201610753136.9 filed on Aug. 29, 2016 which claimed priority to provisional U.S. patent application No. 62/328,171. These two applications are incorporated into herein in their entireties by reference.

BACKGROUND OF INVENTION

Field of Invention

The present application relates to isolation and detection of cells from a sample. In particular, the present application relates to personalized microfiltration of circulating rare cells, e.g. circulating tumor cells (CTCs), for individual subjects.

Description of Related Art

Cancer is a leading cause of mortality worldwide, in which metastasis leads to more than 90% of deaths of cancer patients. Circulating tumor cells (CTCs) are cancer cells that shed from solid tumor and enter peripheral blood. The detection of CTCs from human blood can work as liquid biopsy, which is a relatively non-invasive way of cancer diagnosis and therapy monitoring. Using CTC as a biomarker enables personalized therapy, understanding of metastasis process, and even targeted treatment strategies.

Various membrane-based microfiltration systems have been developed for CTC detection. Though it is well accepted that CTCs are generally larger and less deformable than normal blood cells, by far most reports on these microfiltration systems only focus on size differences (G. Vona, et al. *Am J Pathol*, 2000, 156, 57-63; I. Desitter, et al. *Anticancer Res*, 2011, 31, 427-41; M. Hosokawa, et al. *Analytical Chemistry*, 2010, 82, 6629-35; M. Hosokawa, et al. *PLoS ONE*, 2013, 8, e67466; S. Zheng, et al. *J Chromatogr A*, 2007, 1162, 154-61; R. A. Harouaka, et al. *Clin Chem*, 2014, 60, 323-33; L. S. Lim, et al. *Lab Chip*, 2012, 12, 4388-96; S. J. Tan, et al. *Biosens Bioelectron*, 2010, 26, 1701-5; C. T. Lim, et al. *Biomed Microdevices*, 2009, 11, 883-92; H. Mohamed, et al. *J Chromatogr A*, 2009, 1216, 8289-95.). The difference of mechanical properties between CTCs and normal blood cells, in terms of cell stiffness or elasticity, has not been utilized in the design of microfiltration system for CTC detection.

Systematic studies including theoretical modeling and simulation, as well as experimental study of CTC capture by microfiltration are of fundamental importance to generate optimized design. However, only a few studies have been devoted to this fundamental work. Few experimental studies have shown the cancer-cell capture results under various microfiltration systems with different filter pore sizes, open factors, flow rates, blood dilutions and sample pre-treatments, without resulting in either a clear design rule or biomechanical studies (F. A. W. Coumans, et al. *PLoS ONE*, 2013, 8, e61774; F. A. W. Coumans, et al. *PLoS ONE*, 2013, 8, e61770; D. L. Adams, et al. *RSC advances*, 2014, 9, 4334-42.). On the other hand, a pure mechanical modeling work has been done to study the CTC passing pressure through five kinds of filter pores with different cross-sections and highlighted the circular cross-section to be the most suitable one for high-efficiency CTC separation (Z. Zhang, et al. *Lab Chip*, 2014.). Tai et al. has proposed a method for highly efficient capturing of cancer cells with high viability, in which only a quantitative method for high viability is clearly provided while a clear design guide for CTC capture with high efficiency and purity is not available (Tai et al., US 2012/0178097 A1). Thus there is still lacking in systematic studies to achieve CTC capture by microfiltration with high efficiency and purity.

All of the existing microfiltration systems for CTC detection from cancer patients apply a certain set of fixed and constant parameters for different patients, regardless of individual differences. The difference in whole blood viscosity between cancer patients and normal control group has been widely reported (A. Pinkowski, et al. bioRxiv, 2015; S. O. Elusoji, et al. *Afr J Reprod Health*, 2008, 12, 84-9; G.-F. von Tempelhoff, et al. *Clin Hemorheol Microcirc*, 2001, 26, 55-61). The treatment for cancer patients, such as chemotherapy and surgery, can also change their whole blood viscosity (A. Pinkowski, et al. bioRxiv, 2015; C. E. Omoti, et al. *Pak J Med Sci*, 2007; M. Khan, et al. *Clin Hemorheol Microcirc*, 1995, 15, 4). The blood viscosity plays an important role in determining optimized parameters of microfiltration system. However, yet a personalized microfiltration system considering individual differences has not been provided.

Therefore, there remains a need to develop methods for achieving CTC capture by microfiltration with high efficiency and purity, as well as a personalized microfiltration method to overcome the above shortcomings. The present invention satisfies these and other needs.

BRIEF SUMMARY OF INVENTION

In an aspect, there is provided in the present application a method of isolating circulating rare cells from a blood sample from a subject, comprising the steps of
- optionally, pretreating the sample to remove at least a portion of red blood cells (RBCs),
- measuring hemorheological parameters of the sample,
- determining filtration parameters based on the measurement of hemorheological parameters; and
- subjecting the sample to microfiltration using the determined filtration parameters.

In some embodiments, the circulating rare cells are circulating tumor cells (CTCs). As compared with circulating tumor cells, leucocytes (white blood cells) account for a higher proportion of cells present in blood, and are smaller in size. As such, the method is suitable for separating circulating tumor cells from leucocytes.

In some embodiments, the subject suffers from a tumor or is suspected of suffering from a tumor. In some embodiments, the subject is mammalian, e.g. human.

In some embodiments, the tumor is selected from the group consisting of breast cancer, cervical cancer, kidney cancer, head and neck cancers, esophagus cancer, gastric cancer, colorectal cancer, colon cancer, rectum cancer, liver cancer, gallbladder cancer, cholangiocarcinoma, biliary tract cancer, pancreatic cancer, lung cancer, ovarian cancer, endometrial cancer, vaginal cancer, vulvar cancer, renal cancer, urothelial cancer, prostate cancer, testicular tumor, osteosarcoma, soft-tissue sarcoma, leukemia, myelodysplastic syndrome, malignant lymphoma, adult T-cell leukemia, multiple myeloma, skin cancer, brain tumor, pleural mesothelioma, and unknown primary cancer.

In some embodiments, the pretreating step comprises contacting the sample with a RBC lysis buffer. It should be understood that the pretreating step is optional. In some embodiments, the blood sample is a whole blood sample. In this case, it is advantageous to remove red blood cells (erythrocyte) from the sample as much as possible. In some embodiments, the blood sample has been subjected to a procedure for removing red blood cells. In this case, the pretreating step is not necessary.

One of the objects of the method is to provide efficient isolation of circulating rare cells from a blood sample based on different hemorheological properties of blood samples that vary from subject to subject. To a certain extent, the method provides a personalized strategy for isolating circulating rare cells based on the unique hemorheological property of the blood sample from a given subject.

In some embodiments, the hemorheological parameters include sample viscosity, mean stiffness of circulating rare cells, mean diameter of circulating rare cells, and any combination thereof. It should be understood that there are other available and measurable hemorheological parameters in the art. Any hemorheological parameters can be chosen as long as they are applicable to the methods of the present application.

Filtration parameters to be determined based on the measurement of hemorheological parameters may include many formats of parameters, including, but not limited to flow velocity, filter pore size, opening factor and dimension, and filtration throughput. As understood by a person skilled in the art, filtration parameters can be characterized by various parameters and in various ways. Some parameters are independent, such as filter pore size. Some parameters, e.g., filtration throughput, depend on a series of other parameters. Therefore, filtration parameters in the present application can be understood in a general way and can include any appropriate combinations of parameters involved in a filtration procedure.

The inventors establish a parameter, i.e., capillary number (Ca) as shown below which can be used to predict the filtration efficiency:

$$Ca = \frac{\mu V}{\sigma}$$

wherein V is mean flow velocity in the microfiltration step in mm/s, μ is sample viscosity in mPa·s, and σ is mean stiffness of circulating rare cells in mid/m. V, μ and σ can be determined by methods known in the art, including, but not limited to, the exemplary methods described hereinafter.

In some embodiments, the filtration parameters are determined such that capillary number (Ca) is between 0.02 and 0.04, e.g. 0.020, 0.021, 0.022, 0.023, 0.024, 0.025, 0.026, 0.027, 0.028, 0.029, 0.030, 0.031, 0.032, 0.033, 0.034, 0.035, 0.036, 0.037, 0.038, 0.039, 0.040.

In some embodiments, the filtration parameters are determined such that the optimized capillary number (Ca) is between 0.03 and 0.04.

As understood by a person skilled in the art, μ and σ can be and can be determined from the hemorheological parameters of a blood sample. In some embodiments, σ can be a predetermined parameter. As such, with respect to a given Ca, the value of V can be calculated. The resultant V can be embodied in other filtration parameters or combination of parameters as long as the resultant V can be achieved in the filtration step.

The inventors also establish a parameter, i.e., normalized cell diameter d* as shown below which can be used to predict the filtration efficiency:

$$d^* = \frac{d_c}{d_p}$$

wherein $d_c$ is mean diameter of circulating rare cells of interest, and $d_p$ is filter pore diameter. $d_c$ and $d_p$ are present in the same unit.

In some embodiments, the filter pore diameter is approximately ½ of the mean diameter of circulating rare cells, i.e. d* is approximately two. Without to be bound by any particular theories, this configuration is advantageous for filtration efficiency.

In some embodiments, the method further comprises a step of electrically identifying the cells captured in the microfiltration step by electrochemical impedance spectroscopy using Nano-spiked electrodes. This step can be done by way of means known in the prior art, including, but not limited to, the exemplary methods described hereafter.

In some embodiments, the method further comprises a step of electrically detecting proteins and/or miRNAs in exosomes by electrochemical impedance spectroscopy using Nano-spiked electrodes, wherein the exosomes are isolated from the filtrate from the microfiltration step. This step can be done by way of means known in the prior art, including, but not limited to, the exemplary methods described hereafter.

In some embodiments, the method further comprises a step of removing background cells, e.g. leucocytes, from the sample. It should be understood that this step can be arranged at any appropriate timing, e.g. after the pretreatment step, prior to the microfiltration step, and during the microfiltration step (see FIG. 8 for an exemplary embodiment).

In some embodiments, the step of removing background cells comprises providing an affinity coating targeted to the background cells on a filter with pore size sufficiently large for the circulating rare cells to flow through. In some particular embodiments, the affinity coating is based on the binding of an antibody to an antigen present on the surfaces of the background cells. In some particular embodiments, the background cells are leucocytes, and the affinity coating comprises an anti-CD-45 antibody.

In another aspect, there is provided in the present application a method for determining filtration parameters in a microfiltration process for isolating circulating rare cells from a blood sample from a subject, comprising normalization of parameters in microfiltration of cells, theoretical modeling and simulation of cell capturing in microfiltration, phase diagram for capture efficiency and determination of optimized parameters in microfiltration.

In some embodiments, the method is performed on cells from a cell line of the same species as the circulating rare cells. As an exemplary embodiment, where the circulating rare cells to be isolated are breast cancer cells, the method can be performed on cells from an established breast cancer cell line to determine optimized parameters in microfiltration, e.g. capillary number (Ca). Then, the resultant parameters in microfiltration, e.g. capillary number (Ca), can be used or serve as reference in a method for isolating circulating breast cancer cells from a blood sample from a subject.

In another aspect, there is provided in the present application a device for isolating circulating rare cells from a blood sample from a subject, comprising optional pretreatment means for pretreating the sample to remove at least a portion of red blood cells (RBCs), measurement means for measuring hemorheological parameters of the sample, determination means for determining filtration parameters based on the measurement of hemorheological parameters, and microfiltration means for subjecting the sample to microfiltration using the determined filtration parameters.

In another aspect, there is provided in the present application a non-transitory computer storage medium storing a computer program, which when executed by one or more processors, cause the one or more processors to perform operations, wherein the operations comprise receiving hemorheological parameters of a blood sample; determining filtration parameters based on the measurement of hemorheological parameters; and optionally, outputting the filtration parameters.

In another aspect, there is provided in the present application a method of isolating cancer cells from a sample, comprising the steps of measuring hemorheological parameters of the sample, determining filtration parameters based on the measurement of hemorheological parameters; and subjecting the sample to microfiltration using the determined filtration parameters.

In some embodiments, the method includes a step of determining critical Capillary number (Ca*) for the cancer cells according to the methods descried herein. In some embodiments, the critical Capillary number (Ca*) is predetermined. In some embodiments, determining filtration parameters based on the measurement of hemorheological parameters includes selecting filtration parameters such that the Ca of the method is approximate to the critical Capillary number (Ca) for the cancer cells.

DETAILED DESCRIPTION OF THE INVENTION

Several definitions that apply throughout this disclosure will now be presented.

As used herein, the term "circulating rare cells" refers to cells that are not usually present in the circulating system (e.g. blood) of a subject. As an example, "circulating rare cells" may be circulating tumor cells (CTCs) in a subject suffering from a tumor or being suspected of suffering from a tumor.

As used herein, the terms "red blood cell" and "erythrocyte" are used interchangeably, and are understood in a way recognized by a person of ordinary skill in the art.

As used herein, the terms "white blood cell" and "leucocyte" are used interchangeably, and are understood in a way recognized by a person of ordinary skill in the art.

In some models of the present application where tumor cells are to be isolated, the term "capture efficiency" is defined as the percentage of the number of tumor cells captured on device to the number of tumor cells spiked in.

$$\text{Capture efficiency} = \frac{\text{Number of target cancer cells captured on microfiltration device}}{\text{Number of target cancer cells spiked in}} \times 100\% \quad (5)$$

As used in some embodiments, the term "purity" may refer to the percentage of target cancer cells in the total isolated products, for example the percentage of CTCs in the total isolated cells. As this definition is dependent on the number of target cancer cells, in some embodiments, the term "purity" may be represented by the depletion efficiency of leucocytes $\eta_{LD}$, which is defined as $\eta_{LD}=\log(N_i/N_t)$; where $N_i$ is the injected leucocyte number and $N_t$ is the trapped leucocyte number. For example, 1,000 leucocytes trapped on a microfiltration device from $10^7$ injected leucocytes results in 4-log depletion efficiency.

Figure 1:
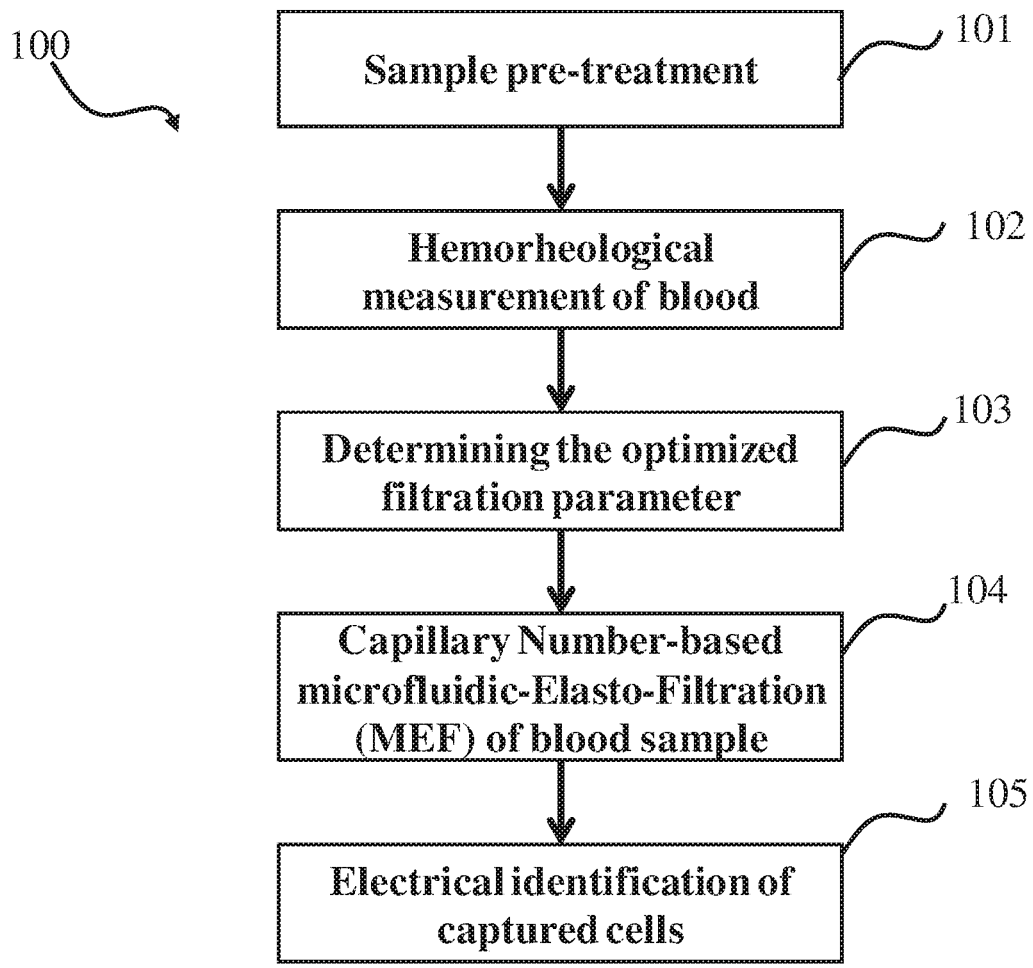
FIG. 1, shown as a flow diagram, represents steps in an exemplary method for isolating circulating rare cells from a blood sample using "Capillary Number based Microfluidic Elasto-Filtration".

FIG. 1 is a flowchart illustrating a process 100 of an exemplary method for isolating circulating rare cells from a blood sample. In the pre-treatment 101, the extracted blood sample is diluted by red blood cell (RBC) lysis buffer to reduce the huge number of RBCs. In one embodiment, 1:1(v/v) dilution ratio is applied resulting in a higher than 70% of RBC lysis efficiency. Hemorheological measurement 102 is then applied to the diluted blood sample. In one embodiment, the hemorheological measurement 102 is using a blood rheometer to measure the viscosity of diluted whole blood. Then the filtration parameters based on measured viscosity can be determined by the step 103 provided by the present invention. Microfiltration of blood sample 104 based on the determined parameters is then be conducted to isolated the circulating rare cells. In one embodiment, the circulating rare cells are CTCs. Then isolated cells can be detected and identified by process 105. In one embodiment, the isolated CTCs are identified from the background leucocytes by immunostaining. In another embodiment, the captured cancer cells can be identified by electrochemical impedance spectroscopy using Nano-spiked electrodes.

Figure 2:
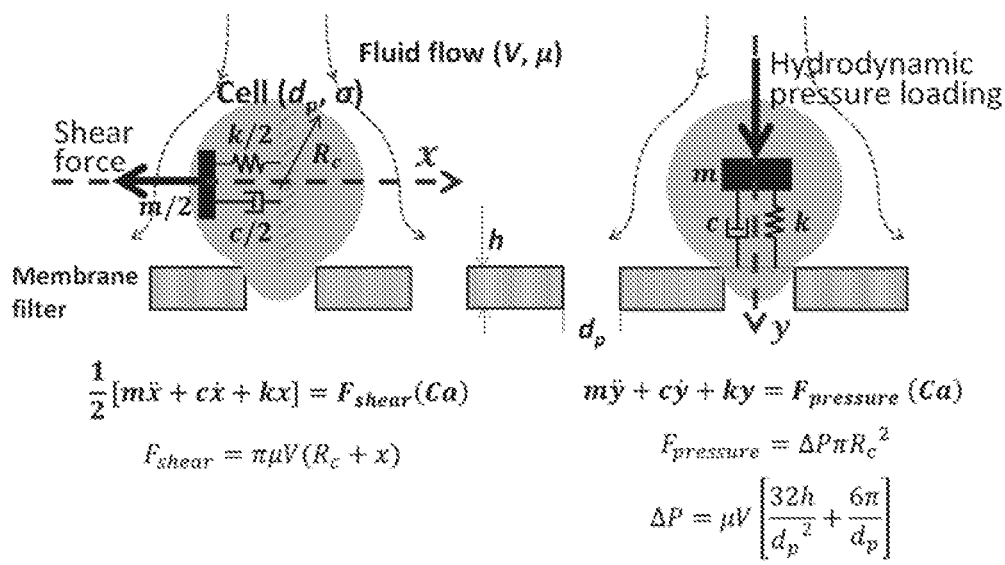
FIG. 2 illustrates a theoretical modeling of cell capturing on a filter pore, in which a cell is modeled as a mass-spring-damper system.

FIG. 2 illustrates a theoretical modeling of capture of cells in microfiltration device. In one embodiment, the cells are CTCs. In another embodiment, the cells are leucocytes. In this simplified two degree-of-freedom (2-DOF) model, the behavior of a cell is modeled as a mass-spring-damper (m-c-k) system to describe the motion of its center of mass.

There are three major parts in capture of cells in microfiltration device, which are the membrane filter, fluid flow and cells. The characteristics of each part have been shown in FIG. 2, in which a competition between viscous forces from fluid flow and cell stiffness, and an interaction between cell and the filter pore, determine whether the cell will be captured in a filter pore on membrane after filtration. The viscous forces from fluid flow are characterized by mean flow velocity V and viscosity $\mu$. The cells are characterized by the cell diameter $d_c$ and stiffness $\sigma$. The membrane filter is characterized by its pore diameter $d_p$.

In order to generalize the parametric study for cell capture in microfiltration devices, the above major parameters are normalized following dimensional analysis. Two dimensionless parameters for characterizing the cell capture have been identified as Capillary number Ca and normalized cell diameter d*, shown as Eq.1 and Eq.2, respectively.

$$Ca = \frac{\mu V}{\sigma} \quad (1)$$

$$d^* = \frac{d_c}{d_p} \quad (2)$$

wherein:
V is the mean flow velocity in microfiltration chamber, and can be present in mm/s;
$\mu$ is the viscosity of fluid flow, and can be present in mPa·s;
$\sigma$ is the stiffness of cell, and can be present in mN/m;
$d_c$ is the cell diameter; !
$d_p$ is the diameter of a filter pore;
$d_c$ and $d_p$ are preferably present in the same unit.

In FIG. 2, a cell is simplified as a mass-spring-damper (m-c-k) system. In the x direction, perpendicular to the fluid flow, a cell experiences a stretching shear force $F_{shear}$:

$$F_{shear} = \pi \mu V (R_c + x) \quad (3)$$

where $R_c$ is the cell radius and x is the displacement of the m-c-k system. Considering the center of mass of the cell as a fixed point, the displacement x, representing the deformation of a half leucocyte, can be characterized by following ordinary differential equation (ODE).

$$\frac{1}{2}(m\ddot{x} + c\dot{x} + kx) = F_{shear} \quad (4)$$

In the y direction along the fluid flow, the cell experiences a hydrodynamic pressure loading $F_{pressure}$ across the filter:

$$F_{pressure} = \Delta P \pi R_c^2 \quad (5)$$

where the pressure drop $\Delta P$ across a membrane filter is:

$$\Delta P = \mu V \left[ \frac{32h}{d_p^2} + \frac{6\pi}{d_p} \right] \quad (6)$$

where h is the height of filter membrane. Considering the contact surface between the cell and the filter pore as a fixed point, the displacement y of a cell can be characterized by following ODE.

$$m\ddot{y} + c\dot{y} + ky = F_{pressure} \quad (7)$$

The shear force $F_{shear}$ and pressure loading $F_{pressure}$ can be expressed as a function of Ca by replacing the fluid viscosity $\mu$ and velocity V using the definition of Ca in Eq. 1. Thus, by solving the two ODEs, Eq. 4 and 7, in x and y directions, the effects of Ca on the formation of a cell pressed against a filter pore can be determined.

Three types of cell lines have been used in the theoretical modeling of capture of cancer cells in microfiltration device. The mass m of cancer cell is estimated by its size and the density of water, which was assumed to be constant during the filtration process. To estimate the damping c of cell, cell was modeled as a cylinder with the same volume of the sphere cell. Thus, damping c was estimated from the apparent viscosity $\mu_c$ of cell using the following equation, $$c = \frac{\mu_c A}{l} \quad (8)$$

in which A is the bottom area and l is the height of equivalent cylinder with the volume same as that of a cell, the spring constant k of cancer cell is chose as the value of cell stiffness σ.

Following table summarizes the parameters used in the theoretical modeling of capture of cancer cells in microfiltration device.

| Parameters in m-c-k model | Cell lines | | |
| --- | --- | --- | --- |
| | HeLa | HEK293 | MCF-7 |
| Cell mass m (ng) | 5.6 | 1.4 | 3.05 |
| Apparent viscosity of cell $\mu_c$ (Pa · s) | 166 | 2000 | 720 |
| Cell damping coefficient c (g/s) | 1.9 | 21.3 | 6.78 |
| Cell stiffness σ or cell equivalent spring constant k (mN/m) | 2.5 | 0.6 | 0.15 |
| Initial cell diameter $d_c$ (μm) | 22 | 14 | 18 |
| Pore size on membrane filter $d_p$ (μm) | 10 | | |
| Thickness of membrane filter h (μm) | 10 | | |
| Capillary number Ca | 0 to 0.04 | | |

Figure 3:
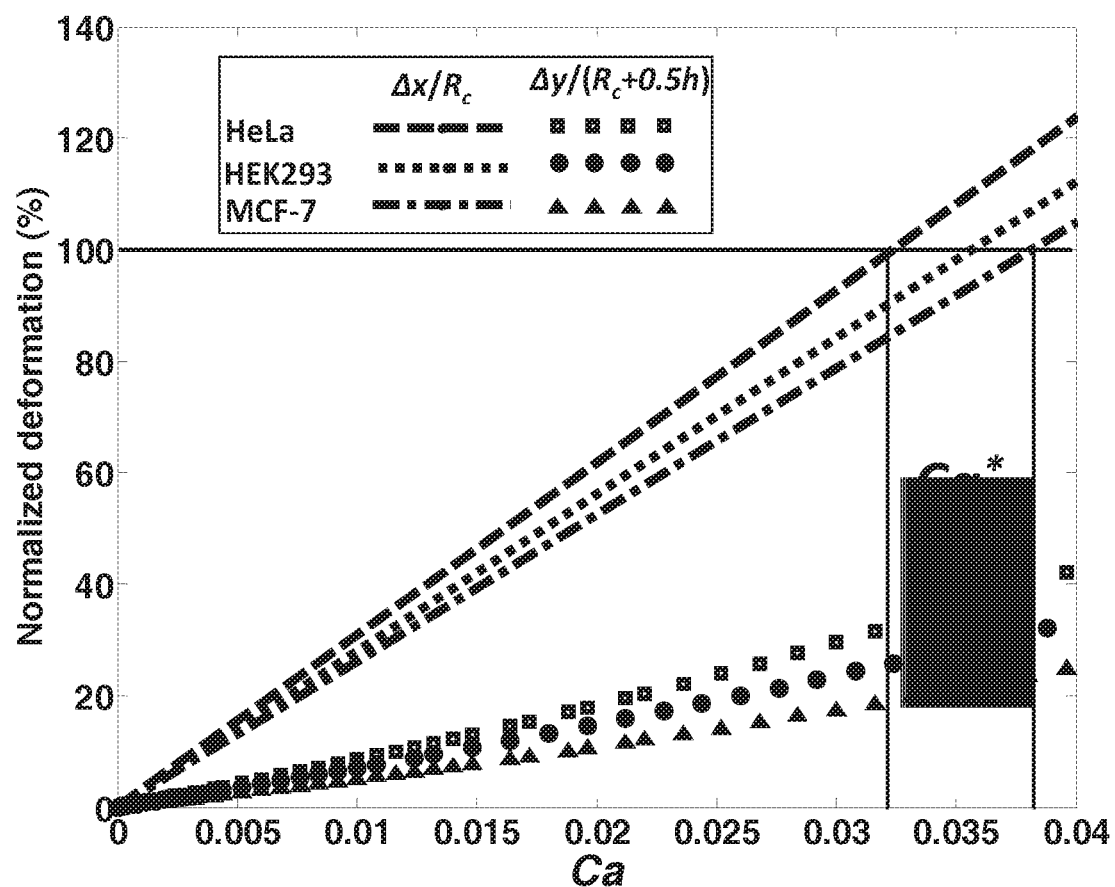
FIG. 3 illustrates the modeling results of normalized cell deformation as a function of Capillary number Ca, wherein critical Capillary number Ca* for enhancing the capture of cancer cells has been identified ranging from 0.033 to 0.038.

By solving the two ODEs, Eq. 4 and 7, in x and y directions, the corresponding deformation of cell as a function of Ca can be determined. FIG. 3 illustrates the deformations of a cell as a function of Ca, Δx and Δy. Here, a cell is considered to be captured in the pore if its center of mass fails to pass the mid-point of the membrane thickness, h, such that: $\Delta y/(R_c+0.5h)<1$. In the Ca range that the normalized deformation in y direction smaller than 1, the cell is still captured on the pore with an elongation in x direction that enhancing the cell capturing. Thus a critical Capillary number for enhancing the capture of cancer cell, corresponding to $\Delta y/(R_c+0.5h)=1$, can be identified. As shown in FIG. 3, the critical Ca for HeLa, HEK293 and MCF-7 cells was 0.033, 0.036 and 0.038, respectively.

The capturing of a leucocyte is also studied by the theoretical modeling of capture of cells in microfiltration device. The neutrophil, constituting more than 60% of leucocytes in human blood with relatively larger size compared with the other four types of leucocytes, is selected as a representative leucocyte in the theoretical model. Following table shows the parameters in the 2-DOF model, in which the mean diameter of leucocytes was measured by a coulter counter (Z2, Beckman Coulter, Inc.) as 6.87±1.28 μm.

| Parameters in m-c-k model | Value |
| --- | --- |
| Leucocyte mass m (ng) | 0.17 |
| Leucocyte damping coefficient c (g/s) | 1 |
| Leucocyte equivalent stiffness k or stiffness σ (mN/m) | 0.03 |
| Initial leucocyte diameter $d_c$ (μm) | 6.87 |
| Pore size on membrane filter $d_p$ (μm) | 10 |
| Thickness of membrane filter h (μm) | 10 |
| Capillary number Ca | 0 to 0.03 |

Figure 4:
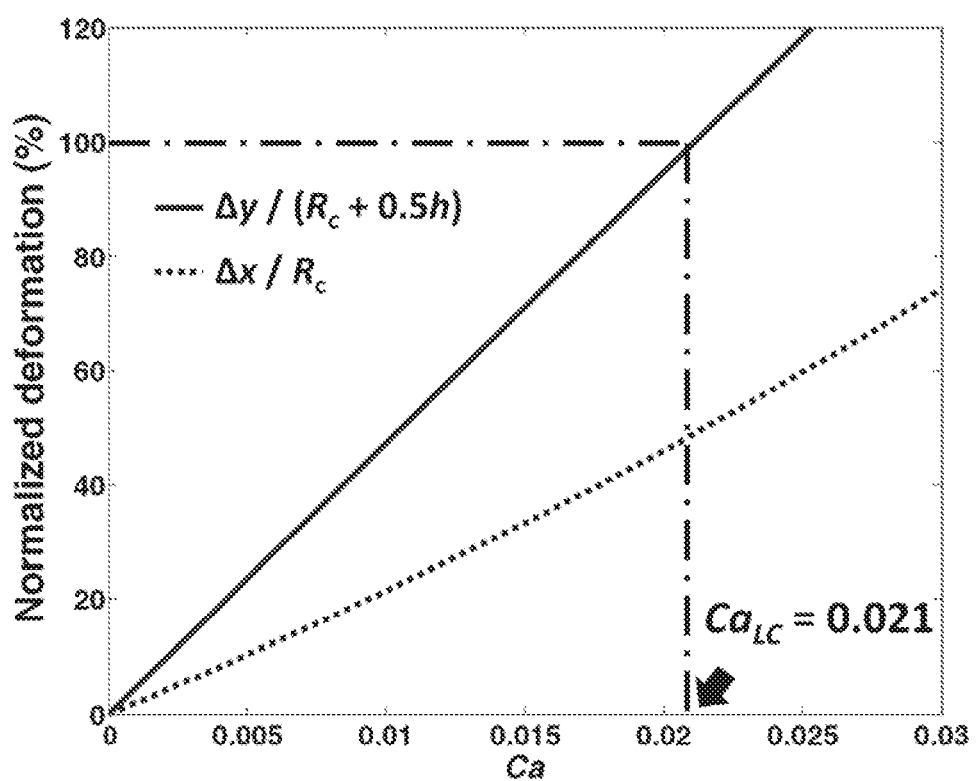
FIG. 4 illustrates the modeling results of normalized WBC deformation as a function of Ca, wherein Capillary number $Ca_{LC}$ for enhancing the capture of WBCs has been identified as 0.021.

FIG. 4 illustrates the deformations of a leucocyte, Δx and Δy as a function of Ca. Here, a leukocyte is considered to be captured in the pore if its center of mass fails to pass the mid-point of the membrane thickness, h, such that: $\Delta y/(R_c+0.5h)<1$, where $R_c$ is the leukocyte cell radius. Thus a critical capillary number for enhancing the capture of leucocytes, corresponding to $\Delta y/(R_c+0.5h)=1$ with $\Delta x/R_c=0.5$, has been identified as $Ca_{LC}=0.021$.

In systematic experimental study for cell capture in microfiltration devices, three types of cell lines have been used because of their different cortical tensions. The cells were cultured using the high-glucose Dulbecco's Modified Eagle Medium (DMEM) (Sigma-Aldrich, USA) supplemented with 10% fetal bovine serum (FBS) (Invitrogen, USA) together with 1% penicillin-streptomycin (Invitrogen, USA), in sterile 10 cm² flasks in an incubator at 5% (v/v) $CO_2$ and at 37° C.

In this set of tests, a constant flow rate of 5 mL/h (Reynolds number <0.1) was applied. Due to the varying opening factors of the membrane filters with different pore sizes, the average velocity V in devices also varies. For the membrane filters with pore sizes of 5, 8, 10 and 12 μm, the average velocity V in the microfiltration devices ranged from 1.6 to 3.2 mm/s.

To adjust the viscosity p of the cell suspension, Polyvinylpyrrolidone (PVP) (Sigma-Aldrich, USA) was added into PBS, which was then used as cell dilution buffer. PVP was used as plasma expander since 1950s. Recently it has been used to alter the plasma viscosity in many biological studies due to its high biocompatibility. Prior to on-chip experimentation, the viability and size of the cells in dilution buffers with PVP at concentrations of 0, 5, 10 and 20 (w/v %) were examined to be not impacted according to fluorescence microscopy. The viscosity p of these cell dilution buffers had been measured by capillary viscometer. The results showed the viscosity ranged from 0.9 to 23.6 mPa·s at 25° C.

As a result, Ca varied over three orders of magnitude between 0.0005 and 0.5 in the present study. To make the Ca more compact and simplify the numerical computations, square root of Ca, i.e., $\sqrt{Ca}$ (sqrt(Ca)), was introduced ranging from 0.02 to 0.7. Following table shows the characteristics of cell lines and parameters in the testing of microfluidic filtration devices for the capture efficiency $\eta_c$ of cells.

| Parameters | Cell lines | | |
| --- | --- | --- | --- |
| | HeLa | HEK293 | MCF-7 |
| Cell mass m (ng) | 5.6 | 1.4 | 3.05 |
| Cell stiffness σ (nN/m) | 2.5 | 0.6 | 0.15 |
| Initial cell diameter $d_c$ (μm) | 22 | 14 | 18 |
| Pore size on membrane filter $d_p$ (μm) | 5, 8, 10, 12 | | |
| Thickness of membrane filter h (μm) | 10 | | |
| Flow velocity V (mm/s) | 1.6 to 3.2 | | |
| Cell suspension (PVP added) viscosity μ (mPa · s) | 0.9 to 23.6 | | |
| Capillary number Ca | 0.00057 to 0.03 | 0.0024 to 0.125 | 0.0095 to 0.5 |
| sqrt(Ca): $\sqrt{Ca}$ | 0.024 to 0.173 | 0.049 to 0.35 | 0.098 to 0.71 |

To harvest the cultured cell lines, the sub-confluent monolayers were dissociated using 0.01% trypsin (Sigma-Aldrich, USA). Cell concentration was determined by manual counting using hemocytometer. Then the cells were re-suspended at a concentration of 1,000 cells/mL into a dilution buffer with certain viscosity.

A cell suspension with a volume of 2 mL (~2,000 cells) was injected into each microfiltration chip using a digital syringe pump, at a flow rate of 5 mL/h. The microfiltration device was placed under a fluorescence microscope (BX41, Olympus, Japan) equipped with a CCD camera. After the filtration is finished, the captured cells were labeled by injecting Acridine Orange/Ethidium Bromide (AO/EB) (Sigma-Aldrich, USA) fluorescence dyes at the same flow rate. The mixture of dyes at 2 μg/mL prospectively with a total volume of 0.5 mL was injected to distinguish between dead cells in red and live cells in green. Phosphate buffer solution (PBS) in 1 mL was then injected at the same flow rate to wash away the redundant dyes. After the flush process, images were then obtained to enumerate the captured cells. The numeration was done by a cell image analysis tool. The capture efficiency was determined as the ratio between the number of captured cells and the total number of injected cells.

Figure 5:
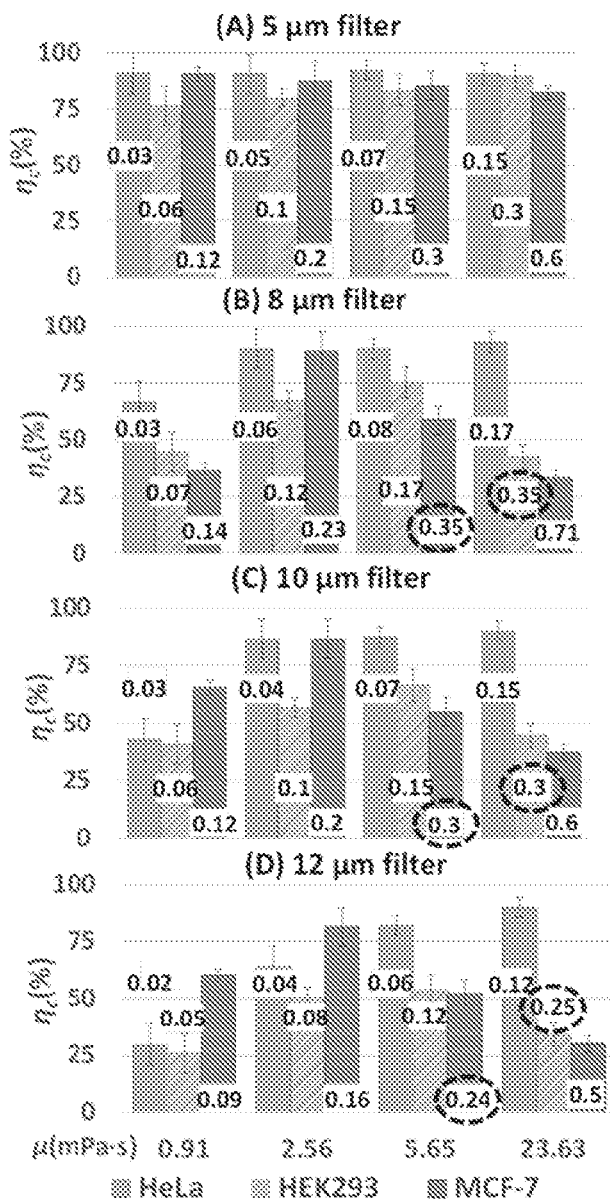
FIG. 5 illustrates the capture efficiency of HeLa, HEK293 and MCF-7 cells using microfiltration devices with different pore sizes and cell suspensions at different viscosities. The square root of Capillary number, sqrt(Ca), in every test is marked on the corresponding column.

FIG. 5 shows the capture efficiency $\eta_c$ of 3 types of cells in suspensions with 4 different viscosities using microfiltration devices with pore sizes of 5, 8, 10 and 12 μm. In the devices with 8, 10 and 12 μm pores on filter, the $\eta_c$ of HeLa cells increased with the increasing cell-suspension viscosity, while the $\eta_c$ of HEK293 and MCF-7 cells initially increased but then decreased with the increasing cell-suspension viscosity. The results indicated that the viscosity difference is not the only mechanism determining the cell capturing on filtration pores. Since the cell types vary in cortical tension, the competition between viscous force and cell cortical tension should be taken into account in the form of Ca.

For the microfiltration devices with 5 μm pores on filter, the capture efficiency did not change much for all 3 types of cells when the viscosity was increased. This is due to the upper limitation of cell deformation, which means even the cell deformed significantly under very high viscosity, it was still captured by the 5 μm pores on filter. Furthermore, in experiments with similar Ca and the microfiltration devices with same pore size, but using different cell types, for example, using the devices with 8 μm filters, the sqrt(Ca) of MCF-7 cells under the viscosity of 5.56 mPa·s and HEK293 cells under the viscosity of 23.63 mPa·s equaled 0.35, the capture efficiency also turned out to be different. Therefore, the sizes of the both filtration pores and cells should also be included as parameters influencing the overall $\eta_c$. Thus the analysis of the experiment results turned out to be consistent with the previous dimensional analysis showing both of these two dimensionless parameters in Eq. 1 and 2 are needed to characterize the capturing of cells on the microfluidic filtration devices.

Figure 6:
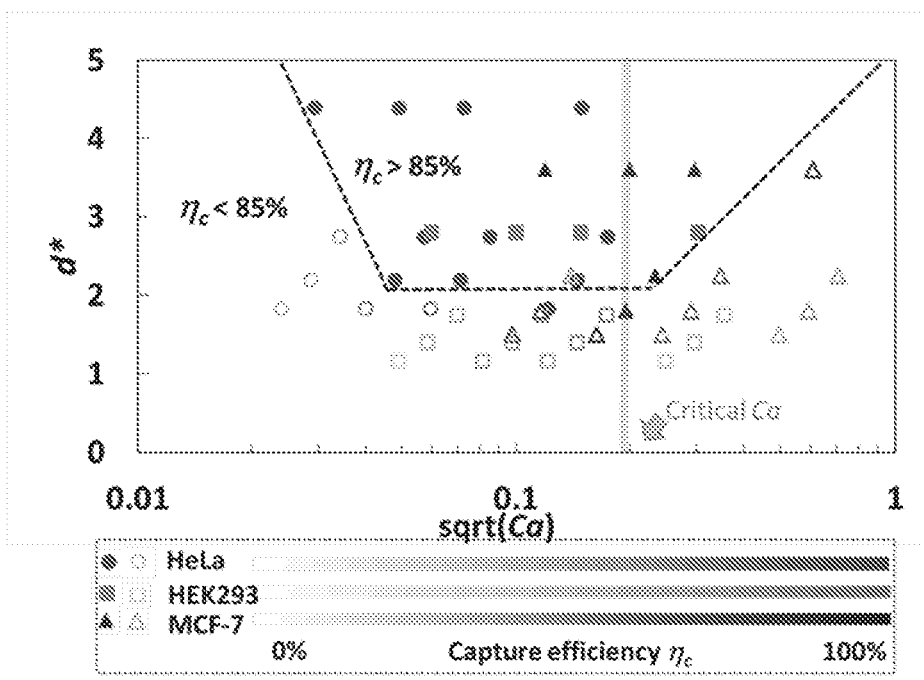
FIG. 6 illustrates the phase diagram for capture efficiency of cancer cells in microfiltration system as a function of the normalized cell diameter and Ca, which can serve as a guide for achieving high capture efficiency in microfiltration systems.

FIG. 6 illustrates a 'Phase Diagram' summarizing the results the capture efficiency of cells as a function of d* and sqrt(Ca). The phase diagram presents the capture efficiency as a function of the normalized cell size d* and sqrt(Ca), in which the values of capture efficiency is indicated by different tones. For HeLa cell, the capture efficiency continually increased in the tested Ca range. For HEK293 and MCF-7 cells, the capture efficiency firstly increased with the increasing Ca, but then decreased after the Ca was larger than a certain value. All of these Ca values turned out to be larger than the corresponding critical sqrt (Ca) for all of the three cell types, which means the capture efficiency only dropped down when the Ca exceeded the critical value that enhanced the cell capturing. Thus, the consistency of our modeling and experimental results has been shown here.

Theoretically, a larger d* would definitely lead to a higher capture efficiency. When dealing with human whole blood samples, however, the purity of captured CTCs should be considered as well. In order to achieve a high purity, the hematologic cells, especially leukocytes (~7 to 12 μm in diameter), are expected to be completely removed from the filter. Thus, the general guideline for achieving both satisfactory capture efficiency and purity is to design the d* around 2 and sqrt(Ca) around 0.2 in microfiltration systems for capturing CTCs from blood samples.

By applying the same experimental method to human leukocytes, the guideline for the capture efficiency of leukocyte can also be generated. In order to achieve a high purity in the isolated CTCs from whole blood, the capture efficiency of leukocytes should be minimized. Thus, together with the guideline for cancer-cell capturing, an integrated guideline for both high capture efficiency and purity can be derived.

The leucocytes were extracted from whole blood samples following a standard protocol. Blood was collected using EDTA-coated tubes (Improve Medical Technology Co. Ltd, China). For each 3 mL of blood, 27 mL of lysis buffer for red blood cells (RBCs) (Sigma-Aldrich, USA) was added and incubated for 20 minutes. The blood samples were then centrifuged for 5 minutes at 2,000 rpm. After centrifugation, the supernatants were aspirated. The leucocyte pellet were re-suspended in 30 mL of PBS and centrifuged for 5 minutes at 2,000 rpm to remove the residual RBCs. After the supernatant aspiration, the leucocyte pellets were re-suspended in dilution buffer with certain viscosity.

Leucocyte concentration was determined by manual counting using hemocytometer (Hausser Scientific, USA). Leucocyte suspensions with a concentration of $10^7$/mL, as the high-normal range in human blood, were prepared to mimic the clinical tests using 1 mL of whole human blood.

Following table summarizes the experimental parameters for studying the depletion efficiency of leucocytes, $\eta_{LD}$, as a function of Ca and normalized leucocyte diameter d* in microfiltration devices. Four types of filters with pore sizes of 5, 8, 10 and 12 μm have been used in the experiments with d* ranging from 1.37 to 0.57. The Ca was adjusted by fixing the flow velocity to be 0.3 mm/s and changing the viscosity of the leucocyte suspension (Reynolds number always <0.1). To adjust the suspension viscosity, a biocompatible polymer, Polyvinylpyrrolidone (PVP) (Sigma-Aldrich, USA), has been added into the PBS solution. Based on previously-reported relationship between PVP concentration in PBS and the viscosity of the corresponding solution, specific amounts of PVP were added into PBS solutions to adjust the viscosity of the leucocyte suspensions and to obtain Ca values of 0.01, 0.015, 0.021 and 0.038.

| Parameters in experiments | Value |
|---|---|
| Initial leucocyte diameter $d_c$ (μm) | 6.87 |
| Pore size of PC filter $d_p$ (μm) | 5, 8, 10, 12 |
| Normalized leucocyte diameter d* = $d_c/d_p$ | 1.37, 0.86, 0.69, 0.57 |
| Cortical tension of neutrophil σ (mN/m) | 0.03 |
| Flow velocity V (mm/s) | 0.3 |
| Cell suspension (PVP adjusted) viscosity μ (mPa · s) | 1, 1.5, 2.1, 3.8 |

-continued

| Parameters in experiments | Value |
|---|---|
| Capillary number Ca = μV/σ | 0.01, 0.015, 0.021, 0.038 |
| Injected leucocyte number | $10^7$ |
| Number of leucocytes left on filter | $N_t$ |
| log depletion of leucocytes $\eta_{LD}$ | $\log(10^7/N_t)$ |

To test the efficiency of leucocyte depletion, 1 mL of leucocyte suspension was injected into the microfiltration devices using a syringe pump at selected flow rates. The leucocyte nuclei were labeled by a fluorescent dye, DAPI (4',6-diamidino-2-phenylindole) (Sigma-Aldrich, USA) before filtration. After the filtration of leucocytes, the MEF CTC chip was placed under a fluorescence microscope (BX41, Olympus, Japan) equipped with a CCD camera. Images of DAPI-labeled leucocytes were then obtained using a 10× objective for cell counting. The number of trapped leucocytes in a microfiltration device was counted by a digital image processing tool.

The depletion efficiency of leucocytes, $\eta_{LD}$, is defined as $\eta_{LD}=\log(N_i/N_t)$; where N is the injected leucocyte number and $N_t$ is the trapped leucocyte number. For example, 1,000 leucocytes trapped in a microfiltration devices from $10^7$ injected leucocytes results in 4-log depletion efficiency. The corresponding leucocyte depletion efficiency has been tested experimentally, under various combinations of d* and Ca.

Under a series of experimental combinations of Ca and d*, the number of trapped leucocytes in microfiltration devices ranged from $10^3$ to $2\times10^4$ resulting in $\eta_{LD}$ ranging from 4 to 2.7. Clogging occurred when Ca was approaching $Ca_{LC}$ in two 5 μm-pore filters. The depletion efficiency in these two tests were estimated by counting the number of pores on the filter resulting in a $\eta_{LD}=2$.

Figure 7:
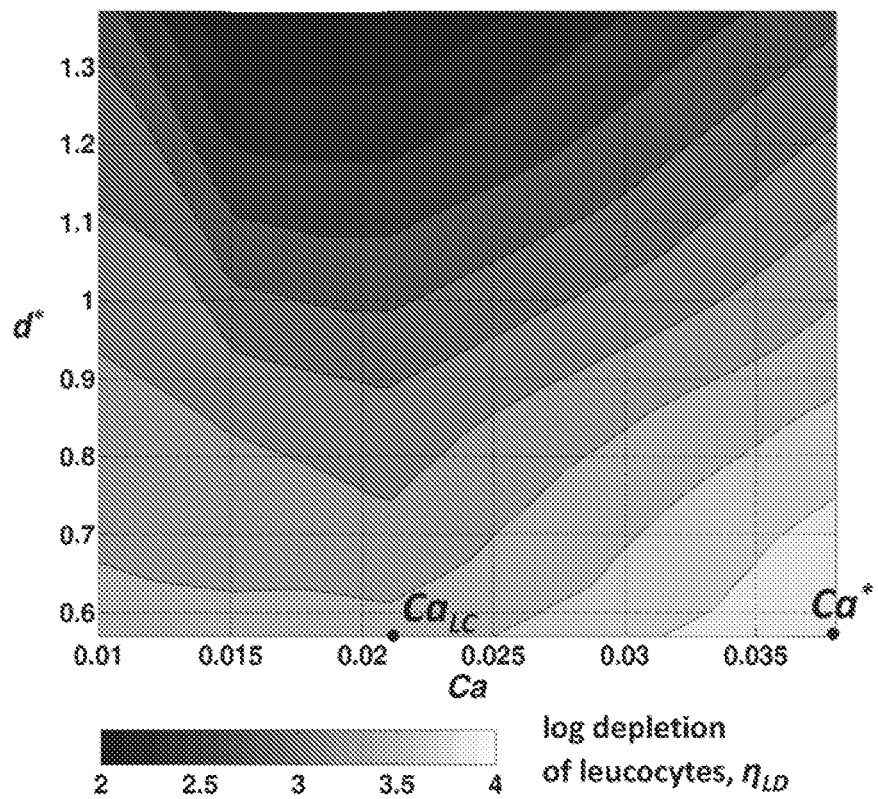
FIG. 7 illustrates the phase diagram for depletion efficiency of WBCs in microfiltration system as a function of the normalized cell diameter and Ca, which can serve as a guide for achieving high depletion efficiency of WBCs in microfiltration systems.

All of the 16 experimental data points have been fitted and presented as a contour plot shown in FIG. 7. For a specific d*, the minimum $\eta_{LD}$ is obtained around $Ca_{LC}=0.021$; this critical level was identified in the analysis of the capture of leukocytes in filter pores. Thus, the calculations based on the theoretical modeling seems to be consistent with the experimental results. As Ca approaches $Ca_{LC}$, the depletion of leukocytes decreases as more leucocytes are captured in microfiltration devices. As a result, when designing a microfiltration system for CTC isolation, it is advantageous to adjust the Ca to be different from $Ca_{LC}\sim0.021$, which will reduce the depletion of leucocytes down to its minimum level.

On the other hand, at the critical Ca*=0.038 for enhancing the capture of cancer cells, $\eta_{LD}$ increases to its maximum value under all of the tested d*. Thus, the capture of cancer cells and leucocytes can be differentiated by tuning the Capillary number. At Ca*≅0.038, the capture of cancer cell is enhanced together with enhanced depletion of leucocytes. As a result, both high capture efficiency and purity of the isolated cancer cells can be achieved. For a microfiltration devices with 8 μm pore size, a close to 4-log depletion of leucocytes has been achieved, which is deemed to be sufficient for molecular characterization of the captured CTCs.

Figure 8:
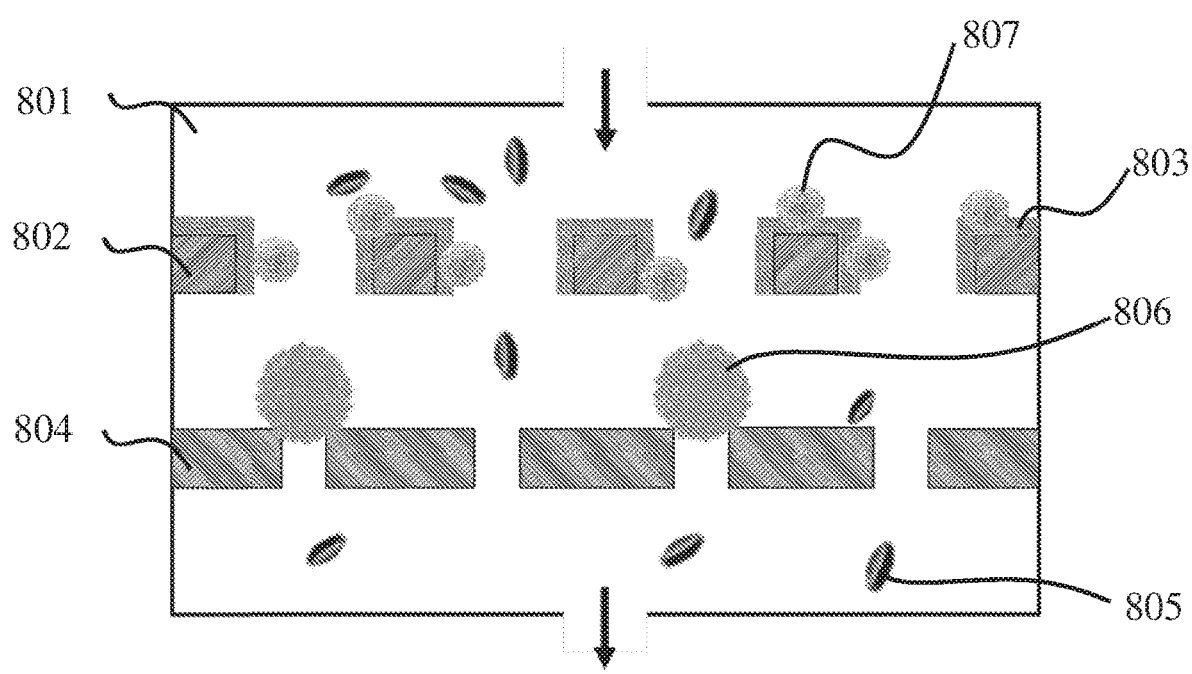
FIG. 8 illustrates the design of a duel-filter microfiltration system for dually depletion of WBCs in microfiltration system to isolate CTCs from a blood sample.

In another aspect, the invention provides a duel-filter microfiltration system 801 for dually depletion of WBCs in microfiltration system to isolate CTCs from a blood sample, illustrated in FIG. 8. In this method, the first filter with larger pore size 802 is first coated with an antibody monolayer 803 which is targeted to WBCs. The secondary filter 804 is designed based on the above method for optimized capture efficiency of CTCs. Thus by applying the two filters in a microfiltration system, the RBCs 805 will pass through the two filters while the WBCs 807 will adhere to the first filter 802 with CTCs 806 captured on the secondary 804. This duel-filter microfiltration system 801 can achieve higher purity of isolated CTCs without reducing the capture efficiency.

In another aspect, the invention provides nano-spike bio-impedance sensor (nBIS) for label-free detection and phenotyping of cancer and non-cancer cells. 3D self-aligned nano-spike arrays were fabricated on a thin aluminum substrate using nano-imprint and scalable electrochemical anodization and etching processes. nBIS can detect impedance of cancer and non-cancer cells without surface functionalization by using the nano-interaction force between the nano-spikes and cell membrane.

Figure 9A:
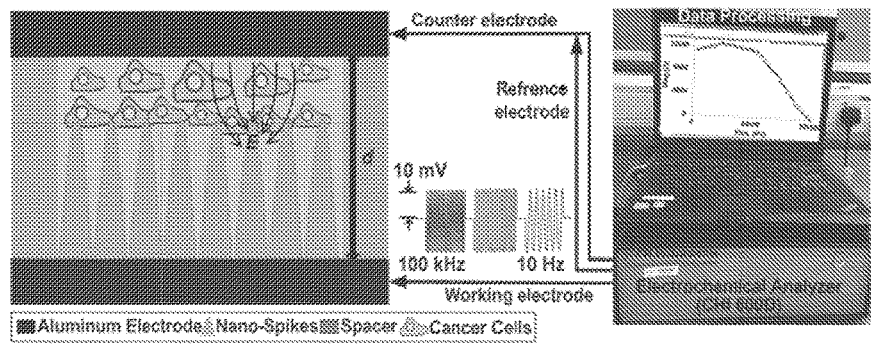
FIGS. 9A to 9D illustrate the identification of cancer cells by electrochemical impedance spectroscopy using Nano-spiked electrodes. (A) Set-up. (B) Bode plots of cancer and non-cancer cells at the concentration of $10^8$ cells/mL, (B) impedance magnitude and impedance phase. (C) Modified Randle's equivalent circuit used for impedance data fitting and parameter extraction. (D) The normalized charge transfer resistance, $R_{ct}$, of cell medium and cancer/non-cancer cells.

FIG. 9A illustrates the schematic diagram of nano-spike based bio-impedance sensor (nBIS). 3D self-aligned arrays of nano-spikes were fabricated on low cost Al foil substrates using nano-imprinting, scalable electrochemical anodization and etching processes. The substrates with fabricated nano-spikes had a thickness of 250 μm and an area of 7×7 mm². nBIS was fabricated after placing a spacer with a height of 100 μm between two electrodes to form a micro-cavity for cell suspension loading. Electrochemical impedance spectroscopy (EIS) was carried on an electrochemical analyzer (CHI 600D, CH Instruments, Inc., USA) with two-electrode setup. Nano-spike electrode was connected to the working electrode, while the counter and reference electrodes of this analyzer were connected to the top electrode. A sinusoidal signal with a modulation voltage of 10 mV and scanning frequency of 10 Hz-100 kHz with zero bias potential was applied to nBIS. Impedance spectra of cancer/non-cancer cells on nBIS were measured using AC impedance and represented as Bode plots.

Figure 9B:
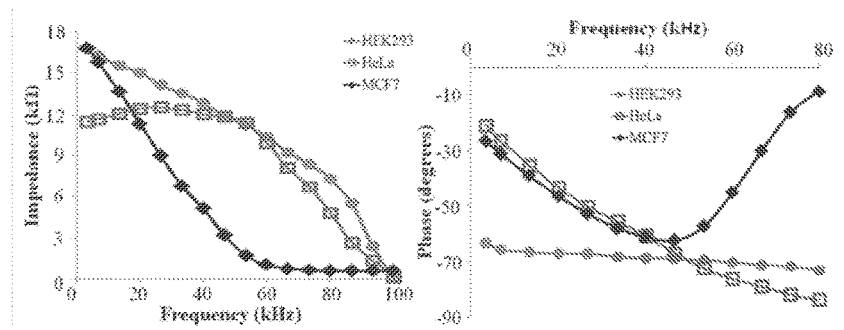

FIG. 9B illustrates cancer/non-cancer cells can be clearly discriminated by impedance spectra. In general, the impedance magnitude decreased from low to high frequency range for a specific cell type. The normal cells had higher impedance as compared to cancer cells. The phase spectra of normal and cancer cells were distinct. Cancer cells showed lower capacitive behavior as compared to normal ones In addition, the impedance spectrum of HeLa cells is also different from that of MCF-7 cells.

Figure 9C:
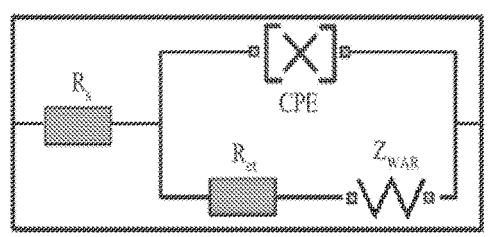

FIG. 9C illustrates the modified Randle's equivalent circuit over the working frequency range. In the equivalent circuit, $R_{ct}$ is the Faradaic charge transfer resistance, $R_s$ is the electrolyte resistance between the two electrodes, CPE is the constant phase element ($Z_{CPE}=1/(Y_0j\omega)^n$) for electrode polarization, and $Z_{WAR}$ is the Warburg impedance related to diffusive ion transport.

Figure 9D:
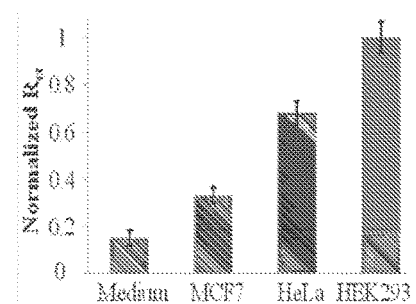

FIG. 9D illustrates the discrimination of different types of cells based on normalized $R_{ct}$. Normal cells had higher normalized $R_{ct}$ as compare to cancer cells. Normalized $R_{ct}$ was also found different among different cancer cell lines, higher for HeLa cells as compare to MCF-7 cells.

Figure 10:
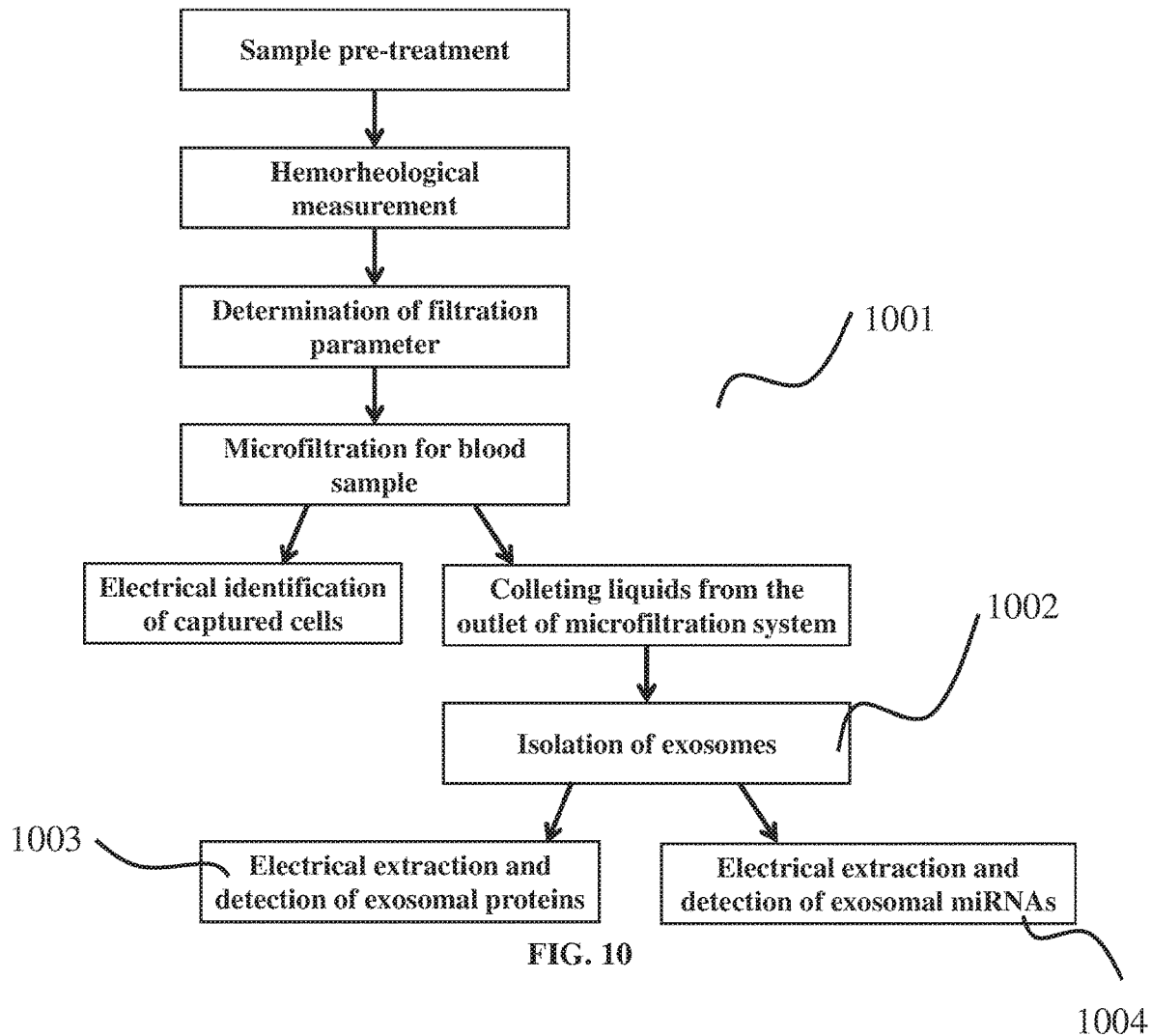
FIG. 10, shown as a flow diagram, represents an exemplary method for isolating circulating rare cells and exosomes from a blood sample.

In another aspect, the invention provides a method for isolating and detection both CTCs and exosomes from blood, as illustrated in FIG. 10. The CTCs can be personalized captured from blood by process 100. The liquid from the outlet of microfiltration system contains exosomes. Thus, after isolating exosomes 1002 from that, the exosomal proteins 1002 and/or exosomal miRNAs 1003 can be extracted and detected by the nano-spike based bio-impedance sensor (nBIS).

EXAMPLES

Example 1

Figure 11:
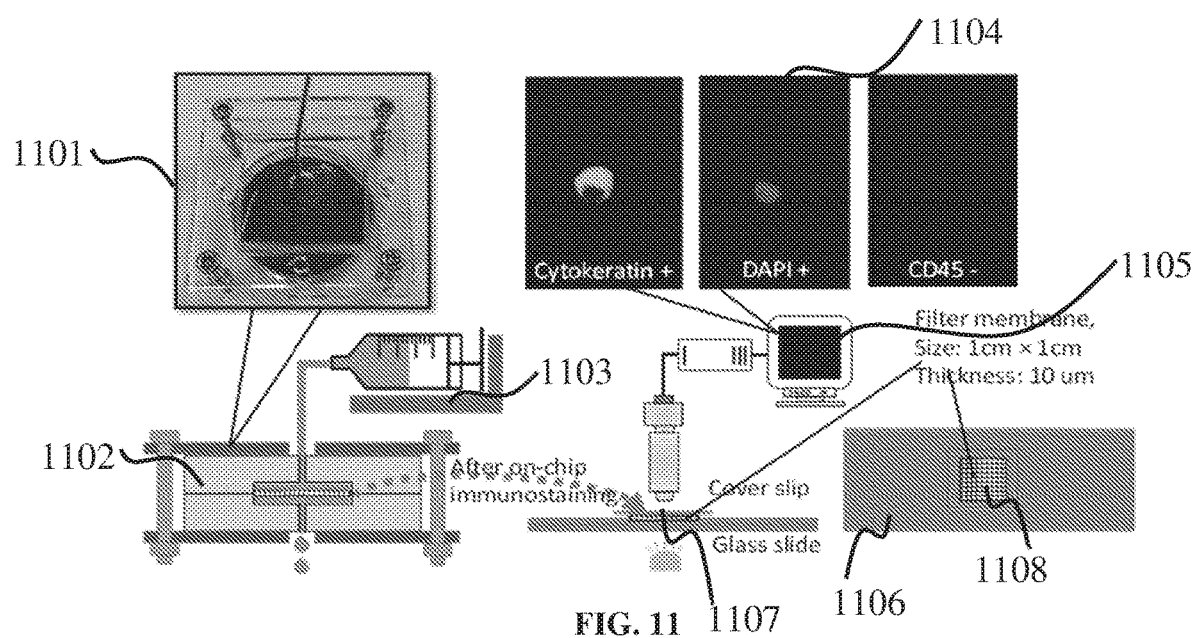
FIG. 11 illustrates the steps for detecting cancer cells/CTCs in a predesigned personalized microfiltration system, including blood filtration under the personalized flow rate, on-chip immune-staining, fluorescence microscopy and image processing.

Illustration of Capturing Cancer Cells Spiked in Blood Sample with High Efficiency and Purity FIG. 11 illustrates the operation of microfiltration system for capturing cancer cells/CTCs in a blood sample. The filter 1108 with predesigned pore size is packaged in a filtration chamber to be a microfiltration chip 1102. The picture 1101 shows a microfiltration chip 1102 during blood filtration. The filtration parameter is determined by the method as described above. A syringe pump 1103 is used to drive the sample into the microfiltration chip 1102. After filtration, the cells captured on filter are labeled by fluorescent dyes. Then the filter 1108 is removed out from the microfiltration chip 1102, and mounted between the glass side 1106 and cover slip 1107. The filter 1108 is observed under a fluorescent microscope. The images 1104 is then obtained for identification and counting of cells by image processing tool 1105.

Here shows an example of applying the provided methods for capturing MCF-7 cells spiked in blood sample with high efficiency and purity. For MCF-7 cells, the stiffness is 0.15 mN/m and the Ca* that can achieve both high efficiency and purity is 0.038. The viscosity of the diluted blood sample was measured as 1.65 mPa·s. Based on the definition of Ca, in Eq. 1, the optimized flow velocity is determined as 3.45 mm/s. The filtration flow rate Q is then determined by $$Q = NS_0 V \quad (9)$$

wherein N is the number of pores on the filter, $S_0$ is the area of each filter pore.

The diameter of MCF-7 cells is around 18 μm. Based on the provided method, the d* is suggested to be around 2. Thus a 8 μm filter is used for capturing MCF-7 cells. Based on Eq. 9, the optimized flow rate is then calculated to be 49 mL/h.

Figure 12:
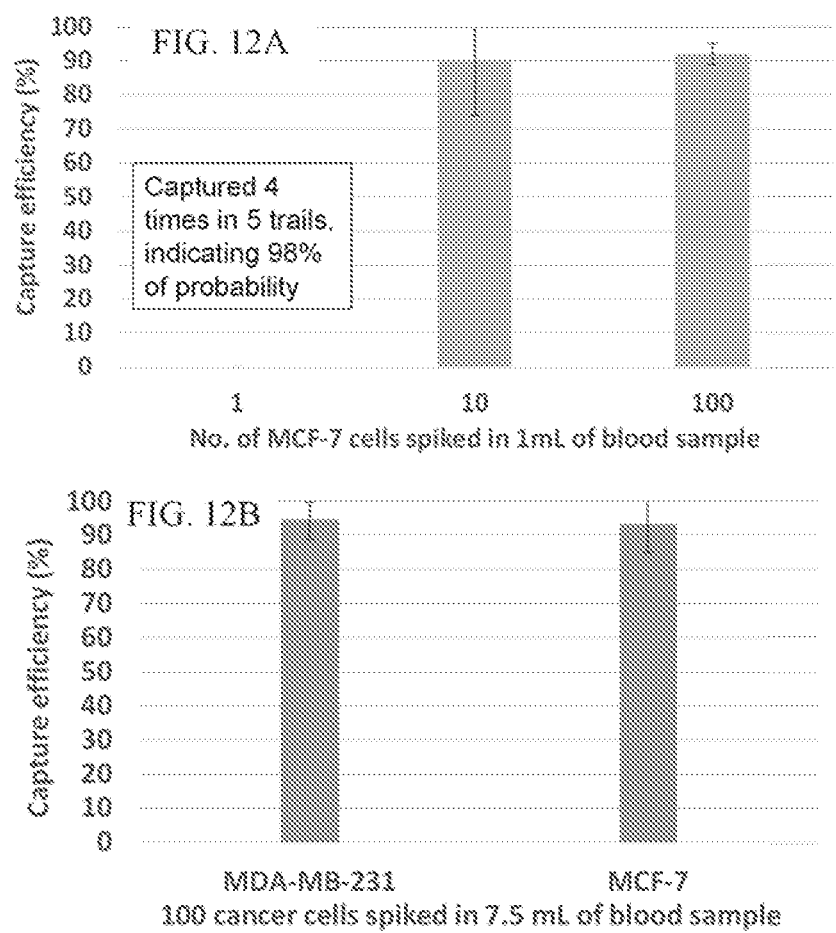
FIGS. 12 A-B illustrate the capture efficiencies of cancer cells spiked into different volumes of blood in the microfiltration system with optimized parameters.

FIG. 12 illustrates the capture efficiency of two types of cancer cell lines spiked into whole blood, using the optimized protocol generated by our previous modeling and experimental work. The capture efficiency for 10 and 100 MCF-7 cells spiked into 1 mL of blood sample showed 90±16% and 92±3.3% respectively. In addition, single MCF-7 has been isolated from 1 mL of blood sample 4 times in total 5 trials, indicating the probability for capturing single cancer cell from 1 mL of blood was as high as 98%. The depletion efficiency was (3.97±0.14)-log, which is sufficient for further molecular assay of captured cancer cells.

In addition, MDA-MB-231 cancer cells, reported as a low EpCAM-expressed type, have been spiked into 7.5 mL of whole blood. The capture efficiency was as high as 94±5.6% for MDA-MB-231 cells. For MCF-7 cells, which is reported to be with higher EpCAM expression, the capture efficiency was also as high as 93±8%. As a result, as a totally physical-property based method, the microfiltration chip can capture more cancer cells from blood than the affinity-based method.

The following table shows the comparison of various indexes between the system of the present application (pMEF chip) with some commercial systems. As shown in the table, pMEF chip is advantageous over the commercial systems in terms of capture efficiency, single CTC capturing probability and purity.

| System | Principle | Capture efficiency (%) | Single CTC capturing probability | Purity(Log-depletion of WBCS) |
|---|---|---|---|---|
| CellSearch ® USA | Immunomagnetic separation | 85 | 65%, 1 cell/mL | 4 |
| Rarecells ®, ISET France | Sized-based filtration | ~70 (MCF-7 cells) | 95%, 1 cell/mL | 3.69 |
| CellSieve Ltd, Singapre | | 81 (MCF-7 cells) | NA | 3.48 |
| pMEF chip | Microfluidic Elasto-Filtration | 92 (MCF-7 cells) (at Ca*) | 98%, 1 cell/mL | 3.97 |

Example 2

Illustration of Personalized Microfiltration Chip (pMFC) for Capturing CTCs in Cancer Patients A two-center clinical trial was initiated to test the performance of pMFCs in isolating CTCs in cancer patients, including in Sun Yat-sen University (SYSU) Cancer Center and Guangzhou First People's Hospital, Guangzhou, China. Twenty-eight patients with colorectal, breast and prostate cancers from stage I to IV and 5 healthy controls have been recruited in this study. Following table shows the summary about the characteristics of patients and healthy controls.

| Characteristics | Cancer patients | Healthy controls |
|---|---|---|
| Gender | | |
| Male | 11 (39.3%) | 5 (100%) |
| Female | 17 (60.7%) | 0 (0%) |
| Age (Median (Range)) | 56 (36 to 83) | 25 (22 to 29) |
| Type of cancer | | |
| Breast | 12 (42.9%) | NA |
| Colon | 15 (53.5%) | |
| Prostate | 1 (3.6%) | |
| Tumor stage | | |
| I | 1 (3.6%) | |
| II | 6 (21.4%) | |
| III | 5 (17.9%) | |
| IV | 16 (57.1%) | |
| Summary | | |
| Total (metastatic and non-metastatic) | 28 (I to IV) | |
| Metastatic | 16 (IV) | |
| Non-metastatic | 12 (I to IIIC) | |
| Early stage | 7 (I to IIB) | |

Blood samples of 10 mL were extracted from patients using CellSave Preservative Tubes (Janssen Diagnostics, USA) under an Institutional Review Board-approved protocol at SYSU Cancer Center. Within 48 hours after extraction, 7.5 mL of each sample was used for the CellSearch® assay and the remaining 2.5 mL was used for pMFC testing. Blood samples of 1.5 mL were extracted from patients using EDTA-coated tubes (Improve Medical Technology Co. Ltd, China) under an Institutional Review Board-approved protocol in Guangzhou First People's Hospital and used for pMFC test within 12 hours. Blood samples from healthy donors were collected using EDTA-coated tubes under an Institutional Review Board-approved protocol.

Figure 13:
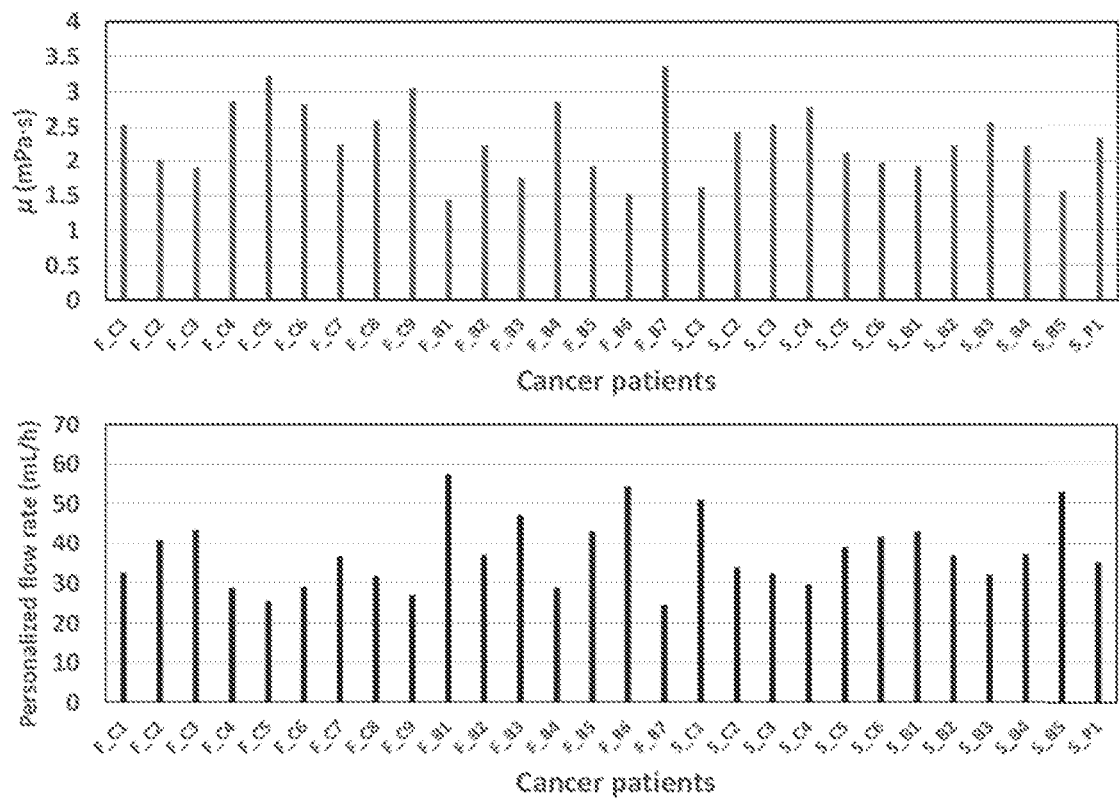
FIG. 13 illustrates the personalized flow rates for the operation of pMFCs based on individual blood viscosity p for the cancer patients in Guangzhou First People's Hospital (F_C1 to F_B7) and SYSU Cancer Center (S_C1 to S_P1).

In clinical study, the blood samples were diluted with red blood cell (RBC) lysis buffer to minimize the impacts from red blood cells (RBCs), in 1:1 (v/v). Then the viscosity of 1 mL diluted blood sample was measured by a blood viscometer (Tangyu Inc., Tianjing, China) calibrated in advance with a series of sucrose solutions with known viscosity. Based on the provided method and the measured sample viscosity, the optimized flow rates can be determined for the microfiltration chips with pore sizes of 8 μm. FIG. 13 shows the measured viscosity of diluted blood samples from the recruited 28 cancer patients. The personalized flow rate for blood filtration was then determined based on the measured viscosity and critical Ca*. The viscosity of the diluted blood samples ranged from 1.44 to 3.36 mPa·s (median 2.25 mPa·s), resulting in a considerable variation in the personalized flow rates ranging from 24.55 to 57.27 mL/h (median 36.7 mL/h).

Under the precisely controlled optimized and personalized flow rate, the rest of the diluted blood samples were filtered in pMFCs. Once blood samples were passed through pMFCs, the captured cells on the filters were washed with PBS at a flow rate of 200 μL/min, which is 10-fold lower than the typical filtration flow rate to minimize the CTC loss during washing. Following fixation, permeabilization and blocking at a flow rate of 20 μL/min, cells were stained with fluorescence dye cocktail containing DAPI, anti-pan-cytokeratin (anti-Pan-CK) antibodies conjugated to Alexa Fluor 488 (1:100, CST, USA) and anti-CD45 conjugated to Alexa Fluor 594 (1:50, Novus, USA) by overnight incubation at 4° C. or 1 hour incubation at 37° C. After incubation, PBS at a flow rate of 20 μL/min was used to wash away the residual dyes. Then the pMFC was disassembled to remove the filter membrane from the chip and mount it between a glass slide and cover slip. Using fluorescence microscopy, the captured CTCs can be identified from WBCs. Consistent with the CellSearch® assay, CTC identification criteria were: (1) cytokeratin positive (CK+); (2) nucleated cell (DAPI+); (3) CD45 negative (CD45−); and (4) cell diameter larger than 4 μm.

Figure 14:
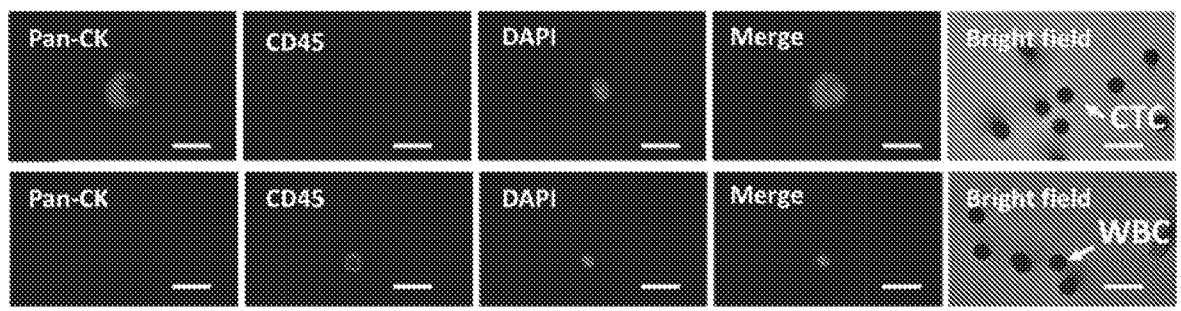
FIG. 14 illustrates a captured CTC and WBC in a pMFC with 8 μm pores after immunofluorescence staining. All scale bars are 20 μm.

Representative micrographs of captured CTCs and WBCs after immunofluorescence staining are presented in FIG. 14, where the cells were trapped in PMFC chips with 8 μm filter pores (All scale bars are 20 μm).

Especially, a competitive study between CellSearch® assay and pMFC method has been conducted using the blood samples from 11 cancer patients with breast, colon and prostate cancers in SYSU cancer center. With the processes shown in the application, ten mL blood was extracted from cancer patient using CellSave Preservative Tubes (Janssen Diagnostics, USA) and used within 48 hours, in which 7.5 mL of blood was used for CellSearch® assay, 0.5 mL was used for viscosity measurement and the rest 2.0 mL was used for pMFC test.

Following table summarizes the CTC detection results using pMFCs for total 28 cancer patients. Overall, more than 1 CTC was detected in 1 or 2 mL blood samples of 19 out of the 28 (67.9%) cancer patients. Particularly, for cancer patients with metastasis, CTCs have been detected in 14 out of 16 (87.5%) patients, while the detection sensitivity was also as high as 41.7% that CTCs in 5 out of 12 patients without metastasis have been detected. Not a single CTC was detected in blood samples of 5 healthy volunteers. The data suggest that no false positives were detected by the pMFC chips. The pMFC method also proved its capability of detecting CTCs even in cancer patients at a relatively early stage, e.g. in two Stage IIB breast cancer patients. In additional, CTCs from cancer patients of early stages have also been detected by pMFCs with 28.6% of sensitivity. Such performances suggested that pMFC is not only useful for monitoring the prognosis or relapse of metastatic cancers, but also with the potential for early detection of cancer.

| Type of cancer | Number of patients | pMFC Patients with CTC |
|---|---|---|
| Breast cancer | 12 (IIB to IV) | 8 (66.7%) |
| Metastatic | 7 (IV) | 6 (85.7%) |
| Non-metastatic | 5 (IIB to IIIA) | 2 (40%) |
| Colorectal cancer | 15 (I to IV) | 10 (66.7%) |
| Metastatic | 8 (IV) | 7 (87.5%) |
| Non-metastatic | 7 (I to IIIC) | 3 (42.9%) |
| Prostate cancer | 1 (IV) | 1 (100%) |
| Healthy control | 5 | 0 (0%) |
| Summary | | |
| Total (metastatic and non-metastatic) | 28 (I to IV) | 19 (67.9%) |
| Metastatic | 16 (IV) | 14 (87.5%) |
| Non-metastatic | 12 (I to IIIC) | 5 (41.7%) |
| Early stage | 7 (I to IIB) | 2 (28.6%) |

Figure 15:
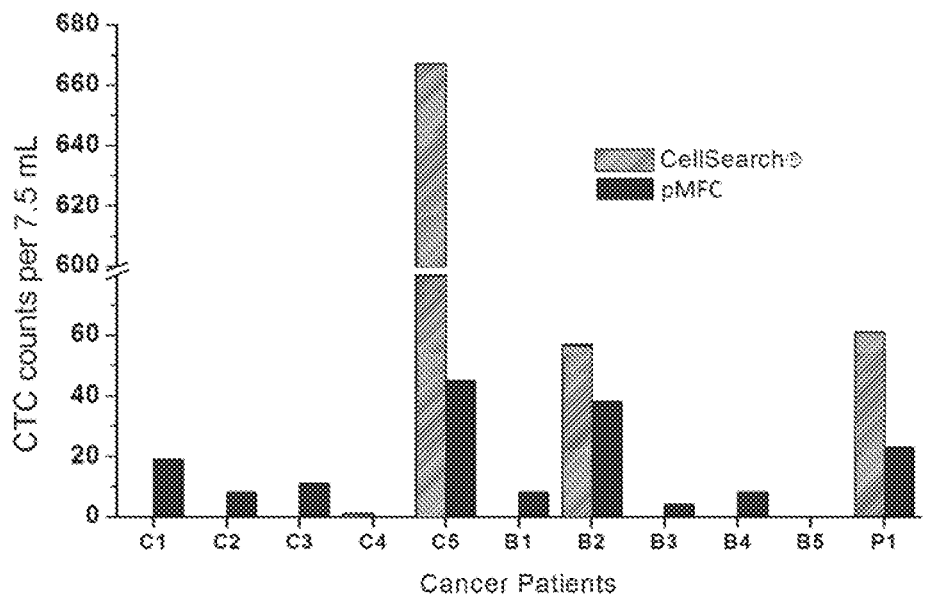
FIG. 15 illustrates the comparison of CTC counts in pMFC technique (normalized from 2.0 to 7.5 mL of blood) and CellSearch® assay for 11 cancer patients.

A comparative study between the performance of the CellSearch® and pMFC methods in CTC detection was carried out with 11 cancer patients in SYSU Cancer Center. The CTC counts are presented in FIG. 15, with the pMFC CTC counts scaled up to that of 7.5 mL blood sample to allow direct comparison (Table 4-5). Using the pMFCs, 1~12 CTCs were detected in 2 mL blood samples of 9 out of the 11 (~82%) cancer patients (with a median value of 3 CTCs in a 2 mL blood sample). Following the CellSearch® assay, 1~667 CTCs were detected in 7.5 mL blood samples of only 4 out of the 11 (~36%) cancer patients (with a median value of 59 CTCs in a 7.5 mL blood sample). Furthermore, using a pMFC, CTCs were detected in a blood sample of a Stage IIB breast cancer patient. Thus, the pMFC technique has been successfully shown to be more sensitive than CellSearch® assay in detecting CTCs from a smaller blood sample (n=11). Also, due to the high false positive results, CTC counts in the CellSearch® assay turned out to be with a much higher variation in these 11 cancer patients (Coefficient of variation (CV %)=265.43>100), with an outlier identified by Grubbs' test (α=0.05).

Following table shows the comparison of sensitivity and specificity in CTC detection using pMFC test and CellSearch® assay. Outperforming the FDA-approved CellSearch® assay, pMFCs showed better sensitivity in both detecting the CTCs from patients in metastatic and non-metastatic cancers with 100% specificity.

| System | Type of cancer | Sensitivity/% | Specificity/% |
|---|---|---|---|
| pMFC | Metastatic | 87.5 | 100 |
| CellSearch ® (cut off: >2 CTCs) | | 35.8* | 99.7* |

-continued

| System | Type of cancer | Sensitivity/% | Specificity/% |
|---|---|---|---|
| pMFC | Non-metastatic | 41.7 | 100 |
| CellSearch ® (cut off: >2 CTCs) | | 14** | 100** |

*W. J. Allard, et al. Clin Cancer Res, 2004, 10, 6897-904.
**L. M. Maestro, et al. Anticancer Res, 2009, 29, 4839-43.

In pMFC, with the measured blood viscosity of each cancer patient, the personalized and optimized flow rate can be determined and applied to achieve uniform and excellent performances of capture efficiency and purity when Ca=Ca*. However, in the non-personalized MFC, the viscosity µ of blood sample is not measured for each cancer patient. Based on optimized Ca for best performances of MFC, a uniform flow rate can be calculated by estimating the µ of each cancer patient as the mean viscosity $\mu_{ref}$ of blood samples from healthy donors. Under such non-personalized conditions, the actual Ca in the MFC for each patient will deviate from the Ca* as $$\text{Actual } Ca = \frac{\mu}{\mu_{ref}} Ca^* \quad (10)$$

Figure 16:
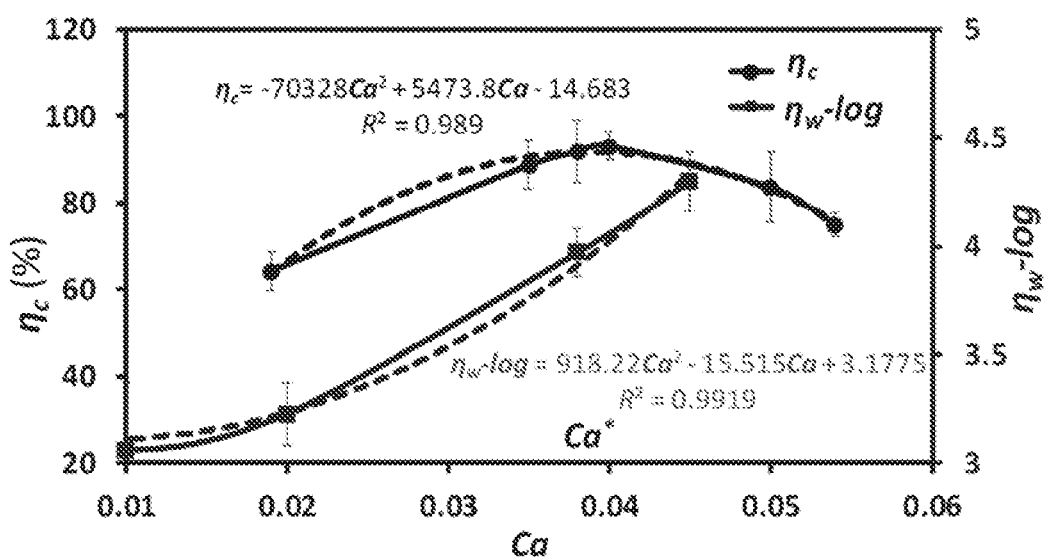
FIG. 16 illustrates the capture efficiency ($\eta_c$) of MCF-7 cells and logarithmic depletion of WBCs ($\eta_w$-log) are fitted as functions of Ca.

Using the following two fitting equations for capture efficiency ($\eta_c$) and logarithmic WBC depletion efficiency ($\eta_w$-log) as a function of Ca, as shown in FIG. 16, the actual values of $\eta_c$ and $\eta_w$-log can be calculated based on the actual Ca values, $$\eta_c = -70328Ca^2 + 5473.8Ca - 14.683 \quad (11)$$

$$\eta_w\text{-log} = 918.22Ca^2 - 15.515Ca + 3.1775 \quad (12)$$

Using the measured viscosity of blood sample from each patient, the actual Ca value can be calculated and subsequently the actual $\eta_c$ and actual $\eta_w$-log can be estimated by Equations (11) and (12) as shown in the following table. There are large variations in the values of $\eta_c$ and $\eta_w$-log for different patients. Thus the uniform and optimized performances of MFC can not be ensured without personalization.

Figure 17:
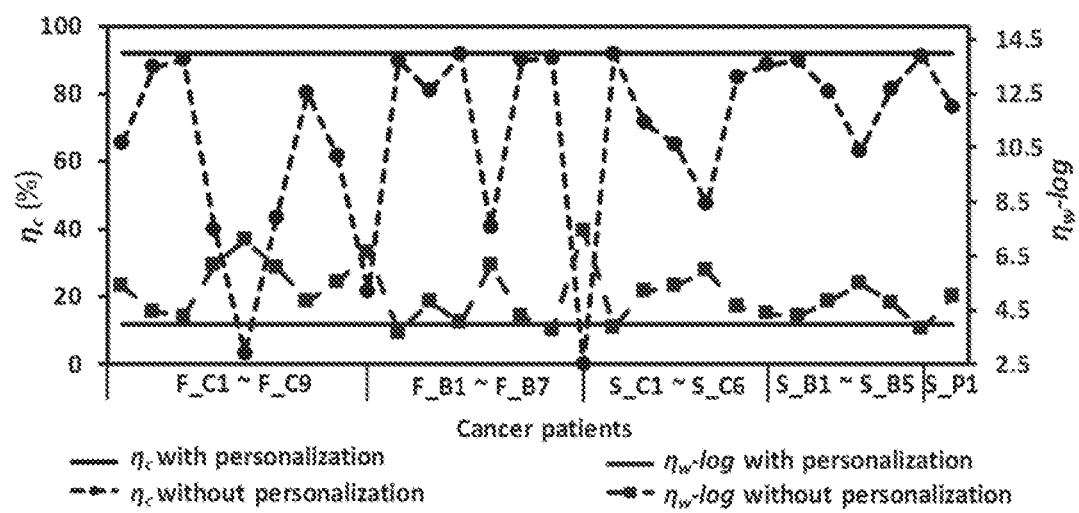
FIG. 17 illustrates the personalization effects on the capture efficiency ($\eta_c$) and logarithmic depletion of WBCs ($\eta_w$-log) in 28 cancer patients.

The personalization effects on $\eta_c$ and $\eta_w$-log using the pMFC method is also depicted in FIG. 17. In the pMFC technique, taking into account the measured individual patient's blood viscosity, the actual Ca for each patient can be manipulated to equal the optimized value Ca* by applying the personalized flow rate. Thus, a high-performance level of the capture efficiency $\eta_c \cong 92\%$ and $\eta_w$-log$\cong 4$ can be achieved, independent of the variations in blood viscosity among individual patients.

| Cancer patients | µ (mPa·s) | $\mu_{ref}$ (mPa·s) | Ca* | Actual Ca | $\eta_c$* | Actual $\eta_c$ | $\eta_w$-log* | Actual $\eta_w$-log |
|---|---|---|---|---|---|---|---|---|
| F_C1 | 2.53 | 1.65 | 0.0389 | 0.058 | 92 | 65.49 | 3.97 | 5.39 |
| F_C2 | 2.02 | | | 0.047 | | 87.76 | | 4.44 |
| F_C3 | 1.9 | | | 0.044 | | 90.18 | | 4.26 |
| F_C4 | 2.87 | | | 0.066 | | 39.87 | | 6.16 |
| F_C5 | 3.23 | | | 0.074 | | 3.34 | | 7.10 |
| F_C6 | 2.83 | | | 0.065 | | 43.33 | | 6.07 |
| F_C7 | 2.25 | | | 0.052 | | 80.12 | | 4.84 |
| F_C8 | 2.59 | | | 0.060 | | 61.60 | | 5.52 |
| F_C9 | 3.06 | | | 0.070 | | 21.79 | | 6.64 |
| F_B1 | 1.44 | | | 0.033 | | 89.50 | | 3.67 |
| F_B2 | 2.23 | | | 0.051 | | 80.94 | | 4.80 |
| F_B3 | 1.75 | | | 0.040 | | 91.69 | | 4.04 |
| F_B4 | 2.86 | | | 0.066 | | 40.75 | | 6.14 |
| F_B5 | 1.92 | | | 0.044 | | 89.85 | | 4.29 |
| F_B6 | 1.52 | | | 0.035 | | 90.75 | | 3.76 |
| F_B7 | 3.36 | | | 0.077 | | 0 | | 7.48 |
| S_C1 | 1.62 | | | 0.037 | | 91.65 | | 3.88 |
| S_C2 | 2.43 | | | 0.056 | | 71.39 | | 5.19 |
| S_C3 | 2.54 | | | 0.058 | | 64.86 | | 5.41 |
| S_C4 | 2.78 | | | 0.064 | | 47.49 | | 5.95 |
| S_C5 | 2.12 | | | 0.049 | | 84.92 | | 4.61 |
| S_C6 | 1.98 | | | 0.046 | | 88.69 | | 4.38 |
| S_B1 | 1.92 | | | 0.044 | | 89.85 | | 4.29 |
| S_B2 | 2.24 | | | 0.052 | | 80.53 | | 4.82 |
| S_B3 | 2.57 | | | 0.059 | | 62.93 | | 5.48 |
| S_B4 | 2.22 | | | 0.051 | | 81.34 | | 4.78 |
| S_B5 | 1.56 | | | 0.036 | | 91.20 | | 3.81 |
| S_P1 | 2.34 | | | 0.054 | | 76.06 | | 5.01 |

On the other hand, when the MFC flow rate is determined based on the average blood viscosity of cohort of healthy donors, without considering the difference in blood viscosity, the MFC will yield large variations in the values of $\eta_c$ and $\eta_w$-log. Obviously, this will result in significant performance reduction of MFCs for clinical applications of CTC detection. Hence, such personalization based on the viscosity of each cancer patient is requested to ensure the optimized performances of MFCs. Thus for all the cancer patients, $\eta_c \cong 92\%$ and $\eta_w$-log$\cong 4$ can be consistently achieved by pMFCs.

Personalized detection provides a more reliable CTC detection performance not only among different cancer patients and cancer types, but also for the same cancer patient under different courses of treatment. Based on the CTC counts using pMFC method, the correlation between CTC enumeration and metastasis progress, treatment outcome and prognosis can be revealed more reliably, regardless of the variations in blood characteristics among different cancer patients, cancer types or for the same cancer patient in different stages. In comparison with other techniques, the pMFC method enables higher CTC detection performance in a wide range of blood samples allowing CTC detection in blood of early-stage cancer patients.

The invention claimed is:

1. A method of isolating circulating rare cells from a blood sample from a subject, comprising the steps of:
   optionally, pretreating the blood sample to remove at least a portion of red blood cells (RBCs),
   measuring hemorheological parameters of the blood sample, wherein the hemorheological parameters comprise sample viscosity (μ) and mean stiffness of circulating rare cells (σ) in the blood sample,
   determining filtration parameters based on the measurement of the hemorheological parameters wherein the filtration parameters are determined such that Capillary number (Ca) as defined below is between 0.02 and 0.04, $$Ca = \frac{\mu V}{\sigma}$$

wherein V is mean flow velocity in a microfiltration step in mm/s, μ is sample viscosity in mPa·s, and σ is mean stiffness of circulating rare cells in mN/m; and
   subjecting the blood sample to microfiltration using the determined filtration parameters.

2. The method of claim 1, wherein the circulating rare cells are circulating tumor cells (CTCs).

3. The method of claim 1, wherein the subject suffers from a tumor or is suspected of suffering from a tumor.

4. The method of claim 1, wherein the pretreating step comprises contacting the blood sample with a RBC lysis buffer.

5. The method of claim 1, wherein the hemorheological parameters further include a mean diameter of circulating rare cells.

6. The method of claim 1, wherein the filtration parameters include filter pore diameter which is approximately ½ of a mean diameter of circulating rare cells.

7. The method of claim 1, further comprising a step of electrically identifying cells captured in the microfiltration step by electrochemical impedance spectroscopy using Nano-spiked electrodes.

8. The method of claim 1, further comprising a step of electrically detecting proteins and/or miRNAs in exosomes by electrochemical impedance spectroscopy using Nano-spiked electrodes, wherein the exosomes are isolated from a filtrate from the microfiltration step.

9. The method of claim 1, wherein subjecting the blood sample to microfiltration further comprises a first step of removing background cells comprising leucocytes, from the blood sample.

10. The method of claim 9, wherein the first step of removing background cells comprises providing an affinity coating targeted to the background cells on a filter with pore size sufficiently large for the circulating rare cells to flow through.

11. The method of claim 10, wherein the affinity coating is based on binding of an antibody to an antigen present on surfaces of the background cells.

12. A device for isolating circulating rare cells from a blood sample from a subject, comprising:
   optional pretreatment means for pretreating the blood sample to remove at least a portion of red blood cells (RBCs),
   measurement means for measuring hemorheological parameters of the blood sample, wherein the hemorheological parameters comprise sample viscosity (μ) and mean stiffness of circulating rare cells (σ) in the blood sample,
   determination means for determining filtration parameters based on the measurement of the hemorheological parameters, wherein the filtration parameters are determined such that Capillary number (Ca) as defined below is between 0.02 and 0.04, $$Ca = \frac{\mu V}{\sigma}$$

wherein V is mean flow velocity in a microfiltration step in mm/s, μ is sample viscosity in mPa·s, and σ is mean stiffness of circulating rare cells in mN/m, and
   microfiltration means for subjecting the blood sample to microfiltration using the determined filtration parameters.

13. A non-transitory computer storage medium storing a computer program, which when executed by one or more processors, causes the one or more processors to perform operations, wherein the operations comprise:
   receiving hemorheological parameters of a blood sample wherein the hemorheological parameters comprise sample viscosity (μ) and mean stiffness of circulating rare cells (σ) in the blood sample;
   determining filtration parameters based on the hemorheological parameters, wherein the filtration parameters are determined such that Capillary number (Ca) as defined below is between 0.02 and 0.04, $$Ca = \frac{\mu V}{\sigma}$$

wherein V is mean flow velocity in a microfiltration step in mm/s, μ is sample viscosity in mPa·s, and σ is mean stiffness of circulating rare cells in mN/m; and
   optionally outputting the filtration parameters; and subjecting the blood sample to microfiltration using the determined filtration parameters.

14. A method of isolating cancer cells from a sample, comprising the steps of:
   measuring hemorheological parameters of the sample wherein the hemorheological parameters comprise sample viscosity (μ) and mean stiffness of circulating rare cells (σ) in the sample,
   determining filtration parameters based on the measurement of the hemorheological parameters, wherein the filtration parameters are determined such that Capillary number (Ca) as defined below is between 0.02 and 0.04, $$Ca = \frac{\mu V}{\sigma}$$

wherein V is mean flow velocity in a microfiltration step in mm/s, $\mu$ is sample viscosity in mPa·s, and $\sigma$ is mean stiffness of circulating rare cells in mN/m; and subjecting the sample to microfiltration using the determined filtration parameters.

* * * * *